United States Patent
Sharifi-Mehr et al.

(10) Patent No.: US 11,058,547 B2
(45) Date of Patent: Jul. 13, 2021

(54) INTERBODY IMPLANT WITH INDEPENDENT CONTROL OF EXPANSION AT MULTIPLE LOCATIONS

(71) Applicant: Howmedica Osteonics Corp., Mahwah, NJ (US)

(72) Inventors: Amir Ali Sharifi-Mehr, Bloomingdale, NJ (US); Oliver Buchert, Franklin Lakes, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 11 days.

(21) Appl. No.: 16/592,990

(22) Filed: Oct. 4, 2019

(65) Prior Publication Data
US 2020/0100905 A1  Apr. 2, 2020

Related U.S. Application Data

(63) Continuation of application No. 15/702,171, filed on Sep. 12, 2017, now Pat. No. 10,470,891.
(Continued)

(51) Int. Cl.
*A61F 2/46* (2006.01)
*A61F 2/44* (2006.01)
*A61F 2/30* (2006.01)

(52) U.S. Cl.
CPC ............ *A61F 2/4425* (2013.01); *A61F 2/441* (2013.01); *A61F 2/447* (2013.01); *A61F 2/4455* (2013.01);
(Continued)

(58) Field of Classification Search
CPC ....................... A61F 2/44; A61F 2/4455; A61F 2/4465–447; A61F 2/46; A61F 2/4611;
(Continued)

(56) References Cited

U.S. PATENT DOCUMENTS 3,875,595 A  4/1975  Froning
4,932,975 A  6/1990  Main et al.
(Continued)

FOREIGN PATENT DOCUMENTS

CN  1756516 A  4/2006
CN  101610741 A  12/2009
(Continued)

OTHER PUBLICATIONS

Milz et al., U.S. Appl. No. 15/481,854, filed Apr. 7, 2017.
Extended European Search Report of EP 17 19 0437 dated Jan. 11, 2018.

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

Expandable spinal interbody implants include a body and at least one extendable support element connected thereto. Such an implant may include a second extendable support element and a tool selectively positionable with respect to the implant so as to independently or simultaneously expand both extendable support elements. In another example, such an implant may include, at each of a first and second location, a respective movable member and a respective locking element. The at least one extendable support element may be actuatable to expand so as to induce movement of at least one of the movable members away from the body. The locking elements at each of the first and second locations may be selectively lockable such that, when locked, the locking element restrains movement of the associated movable member at that location away from the body without restraining movement of the other movable member away from the body.

20 Claims, 16 Drawing Sheets

Related U.S. Application Data

(60) Provisional application No. 62/393,380, filed on Sep. 12, 2016.

(52) U.S. Cl.
CPC ... *A61F 2/4611* (2013.01); *A61F 2002/30224* (2013.01); *A61F 2002/30405* (2013.01); *A61F 2002/30476* (2013.01); *A61F 2002/30522* (2013.01); *A61F 2002/30523* (2013.01); *A61F 2002/30538* (2013.01); *A61F 2002/30548* (2013.01); *A61F 2002/30556* (2013.01); *A61F 2002/30579* (2013.01); *A61F 2002/30586* (2013.01); *A61F 2002/30601* (2013.01); *A61F 2002/30622* (2013.01); *A61F 2002/30624* (2013.01); *A61F 2002/30828* (2013.01); *A61F 2002/4627* (2013.01); *A61F 2002/4629* (2013.01); *A61F 2002/4692* (2013.01); *A61F 2002/4693* (2013.01)

(58) Field of Classification Search
CPC .................. A61F 2002/30537–30545; A61F 2002/3055–30556
See application file for complete search history.

(56) References Cited

U.S. PATENT DOCUMENTS

| | | |
|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Buttermann |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,527,803 B1 | 3/2003 | Crozet et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,696,751 B2 | 4/2014 | Ashley et al. |
| 8,992,620 B2 | 3/2015 | Ashley et al. |
| 9,028,550 B2 | 5/2015 | Shulock et al. |
| 9,044,218 B2 | 6/2015 | Young |
| 10,182,922 B2 | 1/2019 | Nichols et al. |
| 2001/0056302 A1 | 12/2001 | Boyer et al. |
| 2002/0128716 A1 | 9/2002 | Cohen et al. |
| 2002/0136146 A1 | 9/2002 | Lee et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2003/0130739 A1 | 7/2003 | Gerbec et al. |
| 2004/0030346 A1 | 2/2004 | Frey et al. |
| 2004/0088054 A1 | 5/2004 | Berry |
| 2004/0097928 A1 | 5/2004 | Zdeblick et al. |
| 2004/0133273 A1 | 7/2004 | Cox |
| 2004/0153065 A1 | 8/2004 | Lim |
| 2004/0153156 A1 | 8/2004 | Cohen et al. |
| 2004/0181229 A1 | 9/2004 | Michelson |
| 2004/0186576 A1 | 9/2004 | Biscup et al. |
| 2005/0033437 A1 | 2/2005 | Bao et al. |

(56) References Cited

U.S. PATENT DOCUMENTS

| | | |
|---|---|---|
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0049917 A1 | 3/2006 | Hyde et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0142861 A1 | 6/2006 | Murray |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0241770 A1 | 10/2006 | Rhoda et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1* | 10/2007 | Grotz ............... A61F 2/4611 623/17.11 |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0215153 A1 | 9/2008 | Butterman et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0182343 A1 | 7/2009 | Trudeau et al. |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2010/0324606 A1 | 12/2010 | Moskowitz et al. |
| 2011/0130835 A1 | 6/2011 | Ashley et al. |
| 2011/0137416 A1 | 6/2011 | Myers |
| 2011/0138948 A1 | 6/2011 | Jimenez et al. |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0158071 A1 | 6/2012 | Jimenez et al. |
| 2012/0245695 A1 | 9/2012 | Simpson et al. |
| 2012/0283830 A1 | 11/2012 | Myers |
| 2012/0303124 A1 | 11/2012 | McLuen et al. |
| 2012/0310350 A1 | 12/2012 | Farris et al. |
| 2013/0096677 A1 | 4/2013 | Myers et al. |
| 2013/0103156 A1 | 4/2013 | Packer et al. |
| 2013/0158668 A1 | 6/2013 | Nichols et al. |
| 2013/0158669 A1 | 6/2013 | Sungarian et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204371 A1 | 8/2013 | McLuen et al. |
| 2013/0204374 A1 | 8/2013 | Milella, Jr. |
| 2013/0211525 A1 | 8/2013 | McLuen et al. |
| 2013/0253650 A1* | 9/2013 | Ashley ............... A61F 2/441 623/17.16 |
| 2013/0274883 A1 | 10/2013 | McLuen et al. |
| 2014/0142701 A1 | 5/2014 | Weiman |
| 2014/0277500 A1 | 9/2014 | Logan et al. |
| 2014/0288652 A1 | 9/2014 | Boehm et al. |
| 2014/0316522 A1 | 10/2014 | Weiman et al. |
| 2015/0094814 A1* | 4/2015 | Emerick ............... A61F 2/4611 623/17.16 |
| 2015/0257894 A1 | 9/2015 | Levy et al. |
| 2015/0351925 A1 | 12/2015 | Emerick et al. |
| 2015/0374507 A1 | 12/2015 | Wolters et al. |
| 2016/0089247 A1 | 3/2016 | Nichols et al. |
| 2017/0000622 A1 | 1/2017 | Thommen et al. |
| 2017/0100255 A1 | 4/2017 | Hleihil et al. |
| 2017/0119542 A1 | 5/2017 | Logan et al. |
| 2017/0119543 A1 | 5/2017 | Dietzel et al. |
| 2017/0128226 A1 | 5/2017 | Faulhaber |
| 2017/0333198 A1 | 11/2017 | Robinson |
| 2018/0000606 A1 | 1/2018 | Hessler et al. |
| 2018/0000609 A1 | 1/2018 | Hessler et al. |
| 2018/0071111 A1 | 3/2018 | Sharifi-Mehr et al. |
| 2018/0098860 A1 | 4/2018 | To et al. |
| 2018/0110628 A1 | 4/2018 | Sharifi-Mehr et al. |
| 2018/0116811 A1 | 5/2018 | Bernard et al. |
| 2018/0116812 A1 | 5/2018 | Bernard et al. |
| 2018/0125671 A1 | 5/2018 | Bernard et al. |
| 2018/0147066 A1 | 5/2018 | Daffinson et al. |
| 2018/0193160 A1 | 7/2018 | Hsu et al. |
| 2018/0193164 A1 | 7/2018 | Shoshtaev |
| 2018/0200076 A1 | 7/2018 | Knapp et al. |
| 2018/0243107 A1 | 8/2018 | Foley et al. |
| 2018/0296361 A1 | 10/2018 | Butler et al. |
| 2018/0303621 A1 | 10/2018 | Brotman et al. |
| 2018/0318101 A1 | 11/2018 | Engstrom |
| 2018/0360616 A1 | 12/2018 | Luu |
| 2019/0000646 A1 | 1/2019 | Daffinson et al. |

FOREIGN PATENT DOCUMENTS

| | | |
|---|---|---|
| CN | 101631516 A | 1/2010 |
| CN | 101686860 A | 3/2010 |
| CN | 101686865 B | 5/2013 |
| EP | 1442715 A3 | 11/2004 |
| EP | 1415624 B1 | 5/2006 |
| JP | 2001-518824 A | 10/2001 |
| JP | 2008-502372 A | 1/2008 |
| WO | 2003003951 A1 | 1/2003 |
| WO | 2004016250 A1 | 2/2004 |

(56) References Cited

FOREIGN PATENT DOCUMENTS

| | | | |
|---|---|---|---|
| WO | 2004016205 | A3 | 5/2004 |
| WO | 2006044786 | A3 | 1/2007 |
| WO | 2008011371 | A3 | 3/2008 |
| WO | 2007124078 | A3 | 7/2008 |
| WO | 2008039811 | A3 | 7/2008 |
| WO | 2008112607 | A3 | 12/2008 |
| WO | 2008148210 | A1 | 12/2008 |
| WO | 2009033100 | A1 | 3/2009 |
| WO | 2008121251 | A3 | 8/2009 |
| WO | 2009064787 | A3 | 8/2009 |
| WO | 2009105182 | A1 | 8/2009 |
| WO | 2009114381 | A1 | 9/2009 |
| WO | 2008086276 | A3 | 12/2009 |
| WO | 2010074704 | A1 | 7/2010 |
| WO | 2010068725 | A3 | 10/2010 |
| WO | 2011011609 | A3 | 6/2011 |
| WO | 2011150077 | A1 | 12/2011 |
| WO | 2013119803 | A1 | 8/2013 |
| WO | 2013158294 | A1 | 10/2013 |
| WO | 2016183382 | A1 | 11/2016 |
| WO | 2017117513 | A1 | 7/2017 |

\* cited by examiner

INTERBODY IMPLANT WITH INDEPENDENT CONTROL OF EXPANSION AT MULTIPLE LOCATIONS

CROSS-REFERENCE TO RELATED APPLICATIONS

The present application is a continuation of U.S. patent application Ser. No. 15/702,171 filed Sep. 12, 2017, which claims the benefit of the filing date of U.S. Provisional Patent Application No. 62/393,380 filed Sep. 12, 2016, the disclosures of which are hereby incorporated herein by reference.

BACKGROUND OF THE INVENTION

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of expandable intervertebral implants are disclosed in U.S. Pat. No. 8,992,620 ("the '620 Patent") and in U.S. patent application Ser. No. 15/481,854 filed on Apr. 7, 2017, entitled Expandable Interbody Implant (hereinafter "the '854 Application"), the disclosures of which are hereby incorporated by reference herein as if fully set forth herein.

Although considerable effort has been devoted in the art to optimization of such intervertebral systems and methods, still further improvement would be desirable.

BRIEF SUMMARY OF THE INVENTION

The present invention relates to expandable spinal interbody implants, as well as to systems comprising the same and methods of operating the same.

In accordance with aspects of the invention, a spinal implant for placement between first and second vertebral bodies preferably includes a body and at least first and second extendable support elements connected to the body at respective first and second locations. The body may have a first surface for engaging the first vertebral body. The first and second extendable support elements are each desirably configured to expand such that a respective first and second end of the extendable support element moves away from the body. A spinal implant system comprising such a spinal implant preferably further includes a tool selectively positionable with respect to the implant so as to independently or simultaneously expand the first and second extendable support elements.

According to some further aspects of the above spinal implant system, the spinal implant may be configured to allow the tool to move within the spinal implant to expand the first and second extendable support elements. In some yet further aspects of such spinal implant system, the spinal implant may be configured to allow the tool to move longitudinally within the spinal implant to expand the first and second extendable support elements. According to some even further aspects, such spinal implant may include a channel extending between the first and second extendable support elements, such that the longitudinal movement of the tool is within the channel.

According to some other aspects of the above spinal implant system, each of the first and second extendable support elements may include a piston slidably received within a cylinder. In some yet further aspects of such spinal implant system, the first and second extendable support elements may be configured to be extended by a fluid. According to some even further aspects, the spinal implant may include a channel extending between the first and second extendable support elements. In some such aspects, the tool may supply the fluid to the first and second extendable support elements, and the channel of the spinal implant may be configured to allow the tool to move therealong to selectively supply the fluid to the first and second extendable support elements. In some other of such aspects, the tool may include an internal fluid passageway. In some even further aspects, the channel of the spinal implant may be adapted to receive the tool therein, and, when the tool is received within the channel, an exterior fluid passageway may be defined between an inner surface of the channel and an exterior surface of the tool. That exterior fluid passageway may communicate with the internal fluid passageway via at least one exit port of the tool. In some further aspects of such spinal implant system, the tool may be longitudinally movable along the channel, such that the exterior fluid passageway can be moved to selectively communicate with either or both of the first and second expandable support elements. In some other further aspects of the spinal implant system, the exterior fluid passageway may be defined between a first seal member and a second seal member spaced apart a length of the tool, which seal members may be configured to sealingly engage the inner surface of the channel. In some yet other further aspects of the spinal implant system, the exterior fluid passageway may be at least partially defined by a recessed portion of the exterior surface of the tool.

According to some other aspects of the above spinal implant system, the first end of the first extendable support element and the second end of the second extendable support element may be connected by a plate having a second surface for engaging the second vertebral body. In some yet further aspects of such spinal implant system, the first end of the first extendable support element may be connected to the plate by a first pivotable connection and the second end of the second extendable support element may be connected to the plate by a second pivotable connection.

In accordance with other aspects of the invention, a spinal implant for placement between first and second vertebral bodies preferably includes a body, at least one extendable support element connected to the body, first and second movable members having respective first and second ends movable away from the body, and first and second locking elements. The first movable member and the first locking element are preferably at a first location, and the second movable member and the second locking element are preferably at a second location. The first and second locking elements are desirably selectively lockable such that, when the first locking element is locked, the first locking element restrains movement of the first movable member away from the body without restraining movement of the second movable member away from the body, and, when the second locking element is locked, the second locking element restrains movement of the second movable member away from the body without restraining movement of the first movable member away from the body.

According to some further aspects of the above spinal implant, the first locking element, when locked, may restrain movement of the first movable member away from the body by defining a maximum amount of permitted movement of the first movable member away from the body, and the second locking element, when locked, may restrain movement of the second movable member away from the body by defining a maximum amount of permitted movement of the second movable member away from the body. In some yet further aspects of such spinal implant, the first locking element may be configured to selectively vary the maximum amount of permitted movement of the first movable member away from the body when the first locking element is locked, and the second locking element may be configured to selectively vary the maximum amount of permitted movement of the second movable member away from the body when the second locking element is locked.

According to some other aspects of the above spinal implant, the first and second locking elements may each be rotatable so as to move between a locked configuration and an unlocked configuration. In some yet further aspects of such spinal implant, the first and second locking elements may each have a cylindrical shape defining an open interior space. According to some even further aspects, the extendable support element may include a first extendable support element and a second extendable support element, with the first extendable support element being received within the open interior space of the first locking element, and the second extendable support element being received within the open interior space of the second locking element. In some even further aspects, an inner surface of the first locking element may include a first inner projecting feature, and an outer surface of the first extendable support element may include a first outer projecting feature. The first inner projecting feature and the first outer projecting feature may be arranged to selectively engage and disengage one another based on a rotational position of the first locking element. An inner surface of the second locking element may similarly include a second inner projecting feature, and an outer surface of the second extendable support element may include a second outer projecting feature. The second inner projecting feature and the second outer projecting feature may likewise be arranged to selectively engage and disengage one another based on a rotational position of the second locking element. In some such aspects, the first inner projecting feature, the first outer projecting feature, the second inner projecting feature, and the second outer projecting feature may each include a plurality of projecting ribs. In some other of such aspects, the first inner projecting feature may include a series of first projecting ribs, each of which may extend to a different radial position along the inner surface of the first locking element, and the second inner projecting feature may include a series of second projecting ribs, each of which may extend to a different radial position along the inner surface of the second locking element. According to some aspects, the first locking element may include a plurality of teeth along an outer surface of the first locking element, which teeth may be adapted for engagement by a first control tool to rotate the first locking element so as to move the first locking element between a locked configuration and an unlocked configuration.

According to some other aspects of the above spinal implant, the extendable support element may include a first extendable support element and a second extendable support element, with the first movable member being a portion of the first extendable support element, and the second movable member being a portion of the second extendable support element.

According to some other aspects of the above spinal implant, the first and second movable members may be connected by a plate having a second surface for engaging the second vertebral body. In some yet further aspects of such spinal implant, the first and second movable members are connected to the plate by a respective first and second pivotable connection.

In accordance with yet other aspects of the invention, a spinal implant system may comprise a spinal implant, as described above, and first and second control rods. The first and second control rods are desirably adapted to selectively lock the respective first and second locking elements of the implant.

According to some further aspects of the above spinal implant system, the first and second control rods may be adapted to selectively lock the respective first and second locking element by linear movement of the respective first and second control rod within the spinal implant. In some yet further aspects of such spinal implant system, the first and second control rods may each include a plurality of teeth arranged to engage the respective first and second locking elements so as to control the selective locking of the respective first and second locking elements.

DETAILED DESCRIPTION

Figure 1:
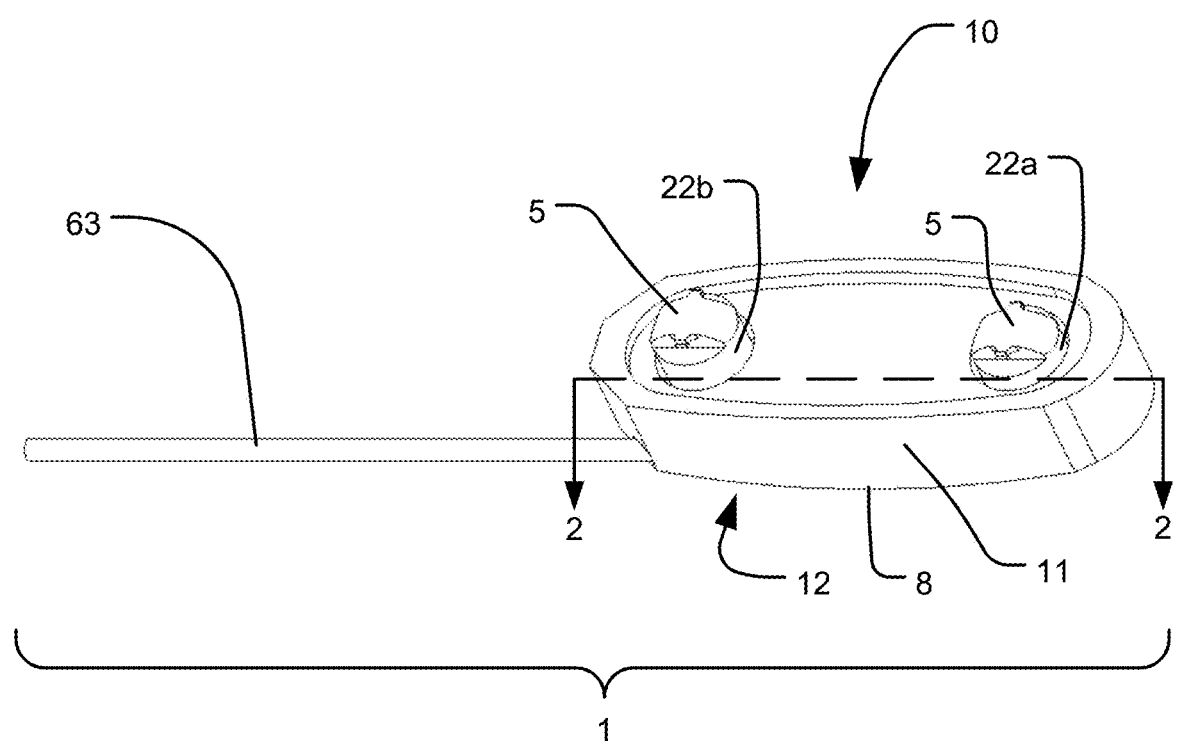
FIG. 1 is a perspective view of a spinal implant system in accordance with one embodiment of the present invention.

FIGS. 1-3 illustrate components of an intervertebral implant system 1 in accordance with an embodiment of the present invention. The system 1 includes an implant 10 having a body or housing 11 and multiple extendable support elements that are expandable such that their top ends 5 are movable away from the housing 11. The extendable support elements may be in the form of any of the extendable support elements disclosed in the '620 Patent or the '854 Application. For example, as shown, the extendable support elements are in the form of pistons 22a and 22b slidably received within a corresponding pair of cylinders 16a and 16b defined within the housing 11. The sliding of the pistons 22a, 22b along the cylinders 16a, 16b results in the translation of the top ends 5 of the pistons 22a, 22b so as to expand the implant 10. The pistons 22a, 22b and cylinders 16a, 16b may operate as part of a hydraulic system, in which the sliding of the pistons 22a, 22b away from the bottoms of the cylinders 16a, 16b is driven by pressurized fluid within the cylinders, as discussed in the '620 Patent and the '854 Application. Although not shown in FIGS. 1-3, the implant 10 may also include a locking system to lock the positions of the pistons 22a, 22b, at least by preventing them from translating back towards the housing 11 once expanded. The locking system may include any of the structures of the locking systems disclosed in the '620 Patent and the '854 Application, and the locking system may also be unlockable to allow the pistons to collapse (e.g., to reposition the implant 10 or to remove it from the body).

Figure 3A:
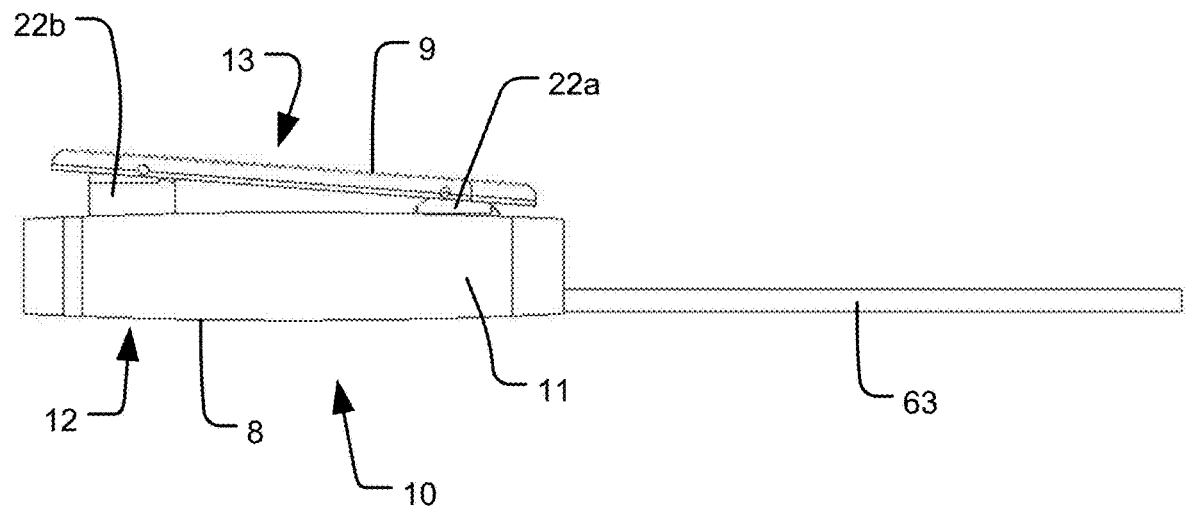
FIG. 3A is a side elevation view of an embodiment of a spinal implant system having a top end plate.
Figure 3B:
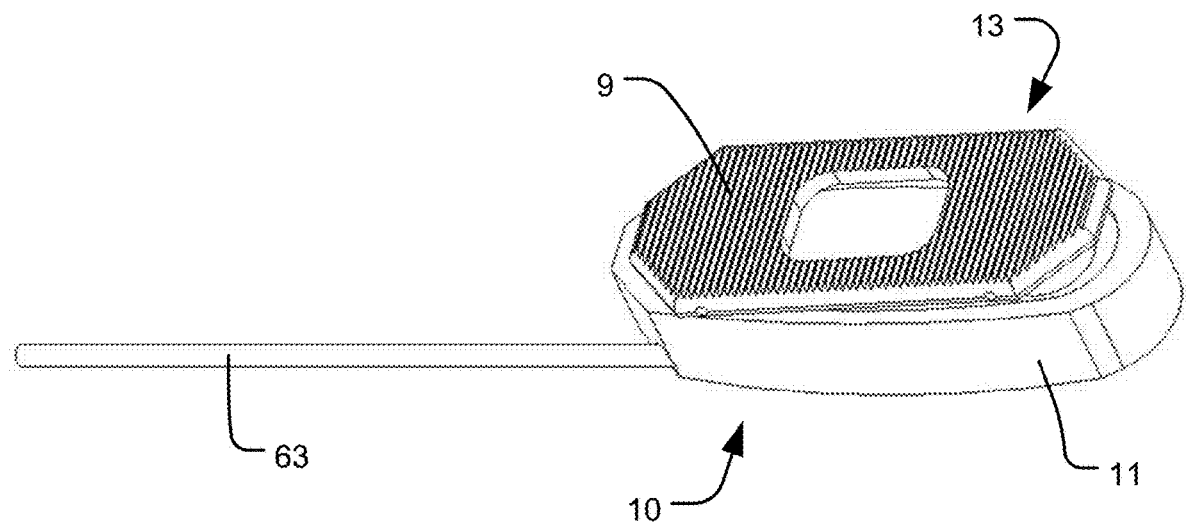
FIG. 3B is a perspective view of the spinal implant system of FIG. 3A.

As discussed below, each extendable support element (e.g., piston 22) can be independently actuated so as to independently expand with respect to the housing 11. The bottom 12 of the housing 11 has a bottom end surface 8, which is a bone engaging surface for engaging a vertebra on one side (e.g., the inferior side) of the intervertebral space within which the implant 10 is positioned. The top ends 5 of the pistons 22a, 22b may represent bone engaging surfaces of the implant 10 for engaging a vertebra on the opposite side of the intervertebral space from the bottom end surface 8 (e.g., the superior side). Alternatively, each piston top end 5 may be connected to a respective plate element (not shown) that has a top end surface representing a bone engaging surface for engaging the vertebra on the opposite side of the intervertebral space from the bottom end surface 8, similar to the plate elements in the embodiment of FIGS. 4-8. In yet a further alternative, both piston top ends 5 may be connected to a common top end plate 13 having a top end surface 9 representing a bone engaging surface for engaging the vertebra on the opposite side of the intervertebral space from the bottom end surface 8, as shown in FIGS. 3A-B. In such an embodiment, the top end plate 13 may be connected to each piston 22a, 22b by a pivotable connection, such as a rotatable pin connection, so that the top end plate 13 can be angled with respect to each piston 22a, 22b to accommodate different amounts of translation of each piston 22a, 22b.

Figure 2A:
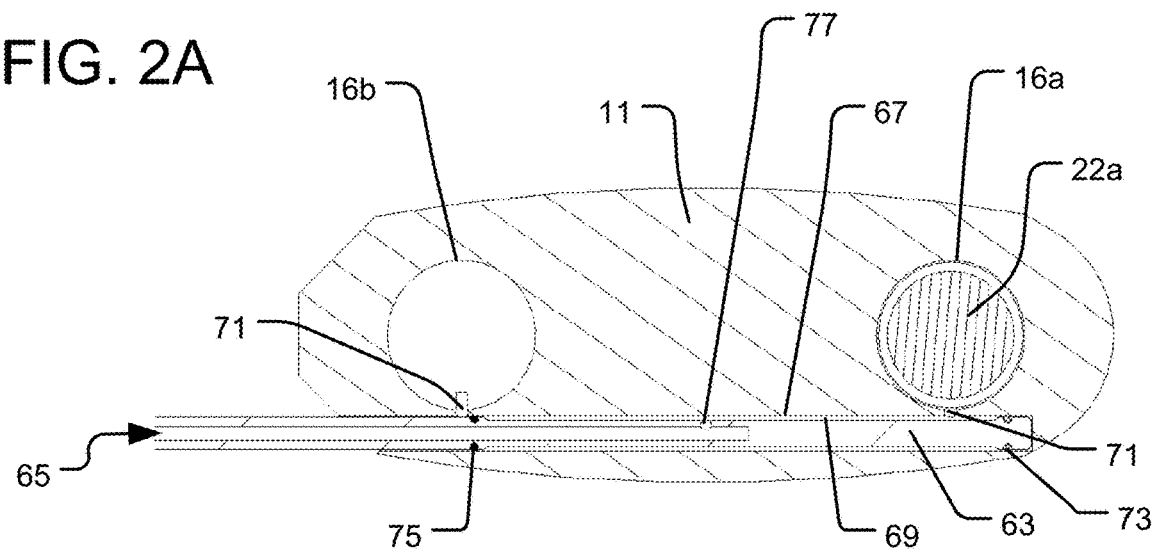
FIGS. 2A-C are cross-sectional plan views about line 2-2 of the embodiment of FIG. 1 in different configurations.
Figure 2B:
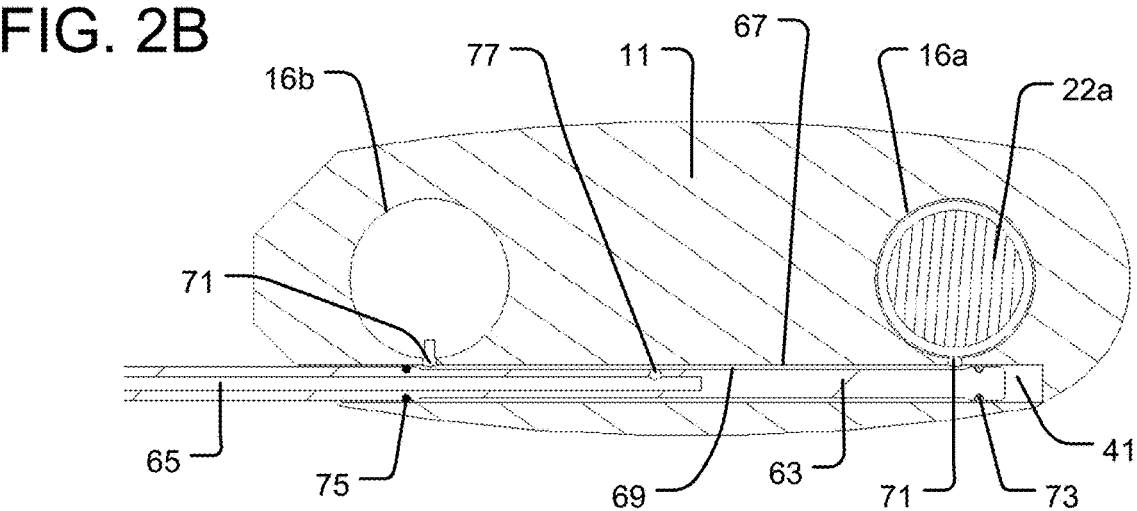
Figure 2C:
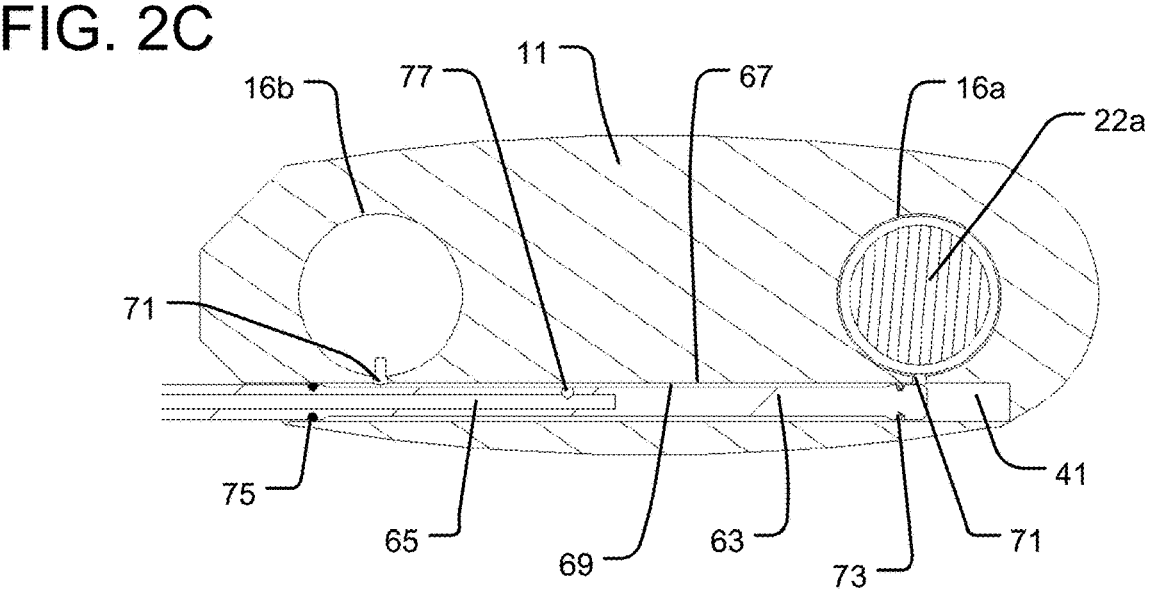

The intervertebral implant system 1 in accordance with the present invention also includes a tool for actuating the expansion of the extendable support elements. The tool may include a fluid delivery cannula 63 for delivering a pressurized fluid to the cylinders 16a, 16b in order to drive the translation of the pistons 22a, 22b. The fluid delivery cannula 63 is in the form of a shaft having an internal fluid passageway 65 extending along its length. The fluid delivery cannula 63 is desirably configured to independently control the expansion of each extendable support element. The fluid delivery cannula 63 may also be configured to control the expansion of both extendable support elements at the same time. For example, the fluid delivery cannula 63 is selectively positionable within a pressure channel 41 extending between both of the cylinders 16a, 16b, which channel 41 communicates with each of the cylinders 16a, 16b via a respective opening 71. The fluid delivery cannula 63 can thus selectively communicate with either or both of the cylinders 16a, 16b based on its longitudinal position within the channel 41. In that regard, when the fluid delivery cannula 63 is received within the channel 41, an exterior fluid passageway 67 is defined between an inner surface of the channel 41 and an exterior surface of the fluid delivery cannula 63. The longitudinal extent of the exterior fluid passageway 67 may be defined by a distal seal member 73, which may be in the form of an o-ring positioned around the exterior surface of the fluid delivery cannula 63 towards its distal end, and a proximal seal member 75, which may also be in the form of an o-ring positioned around the exterior surface of the fluid delivery cannula 63 and spaced proximally from the distal seal member 73. The volume of the exterior fluid passageway 67 may also be defined by a recessed groove 69 within the exterior surface of the fluid delivery cannula 63. As shown in FIGS. 2A-C, that recessed groove 69 may be an annular groove that extends entirely around the circumference of the fluid delivery cannula 63 between the distal and proximal seal members 73, 75. The fluid from the internal fluid passageway 65 may thus be communicated to the external fluid passageway 67 via at least one exit port 77 in the fluid delivery cannula 63.

In order to selectively actuate the extendable support elements, the fluid delivery cannula 63 can be appropriately positioned along the channel 41 as shown in FIGS. 2A-C. That is, as shown in FIG. 2A, when the fluid delivery cannula 63 is positioned at the distal-most end of the channel 41, the external fluid passageway 67 between the distal and proximal seal members 73, 75 communicates with the opening 71 of the distal cylinder 16a, but not with the opening 71 of the proximal cylinder 16b. Thus, the supply of pressurized fluid through the fluid delivery cannula 63 in the position illustrated in FIG. 2A will cause expansion of the distal piston 22a only. By retracting the fluid delivery cannula 63 to the position illustrated in FIG. 2B, the external fluid passageway 67 communicates with the openings 71 of both the distal and proximal cylinders 16a, 16b. Thus, in the position illustrated in FIG. 2B, the supply of pressurized fluid through the fluid delivery cannula 63 will cause expansion of both pistons 22a, 22b. Finally, further retraction of the fluid delivery cannula 63 to the position illustrated in FIG. 2C will cause the external fluid passageway 67 to communicate with the opening 71 of the proximal cylinder 16b but not the distal cylinder 16a. Thus, supply of pressurized fluid through the fluid delivery cannula 63 in the position illustrated in FIG. 2C will cause expansion of the proximal piston 22b only.

By manipulating the fluid delivery cannula 63 as discussed above, the expansion of the different extendable support elements can be individually controlled. That may be useful, for example, in order to adjust the height of each extendable support element to best fit the anatomy of the patient. Individual adjustment may also be useful for providing a specific angular correction to the patient's spine. For example, by providing greater expansion at the anterior portion of the spine than the posterior portion of the spine, the implant 10 may decompress nerve roots while also providing lordosis correction.

The above-described embodiment illustrated in FIGS. 1-3 is desirably structured to be used in a PLIF technique. That is, the generally linear shape of the implant 10 between the distal and proximal ends of the implant may be particularly suitable for inserting two such implants 10 into an intervertebral space (one on either side of the spine) along a posterior to anterior direction, such that the distal end of the implant is positioned more anteriorly with respect to the spine than the more posteriorly positioned proximal end of the implant. However, the same operative components discussed above can also be included in implants structured to be used in a TLIF technique or along a lateral approach. For example, an implant structured to be used in a lateral approach may have a similar configuration to that discussed above, but may be sized to cover a substantial portion of the disc space. As for an implant structured to be used in a TLIF technique, the same operative components discussed above can be incorporated into an implant having an overall kidney bean-like shape. In such an embodiment, the channel for receiving the fluid delivery cannula may be linear between the cylinders, as shown in the above-discussed figures, or it may follow an arcuate path. If the channel is arcuate, the fluid delivery cannula may have a corresponding arcuate shape or may be flexible to conform to the path of the channel.

Although the embodiment of FIGS. 1-3 allows for individual control of the amount of expansion at different locations along the implant 10 by allowing for individual actuation of the extendable support elements positioned at different locations within the implant 10, similar individual control of the amount of expansion at different locations along the implant 10 may be provided in other ways. For example, in the embodiment of FIGS. 4-12, discussed below, the same expansion pressure may be simultaneously applied to the different locations along the implant 110, while those different locations can be individually locked to restrain expansion at the selected location(s) during the application of such expansion pressure.

Figure 4:
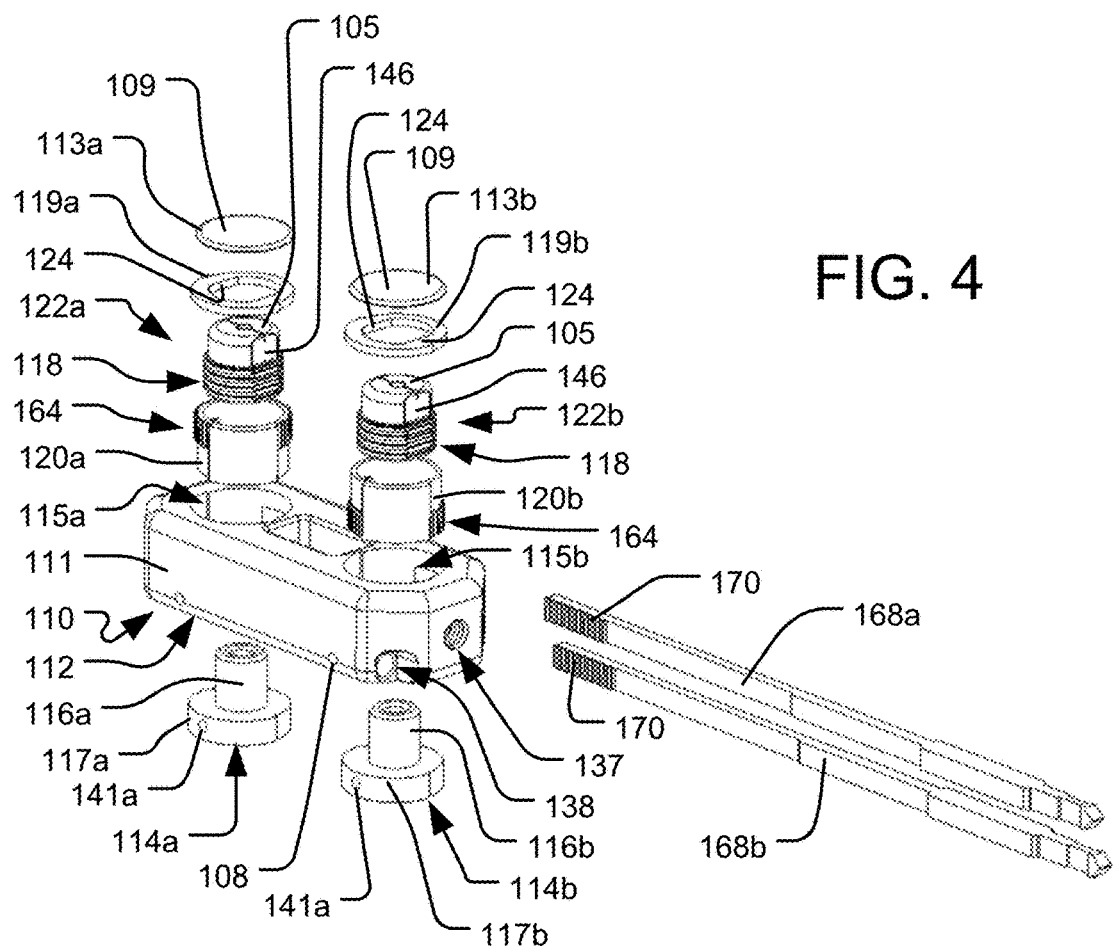
FIG. 4 is an exploded, perspective view of a spinal implant system in accordance with another embodiment of the present invention.
Figure 5:
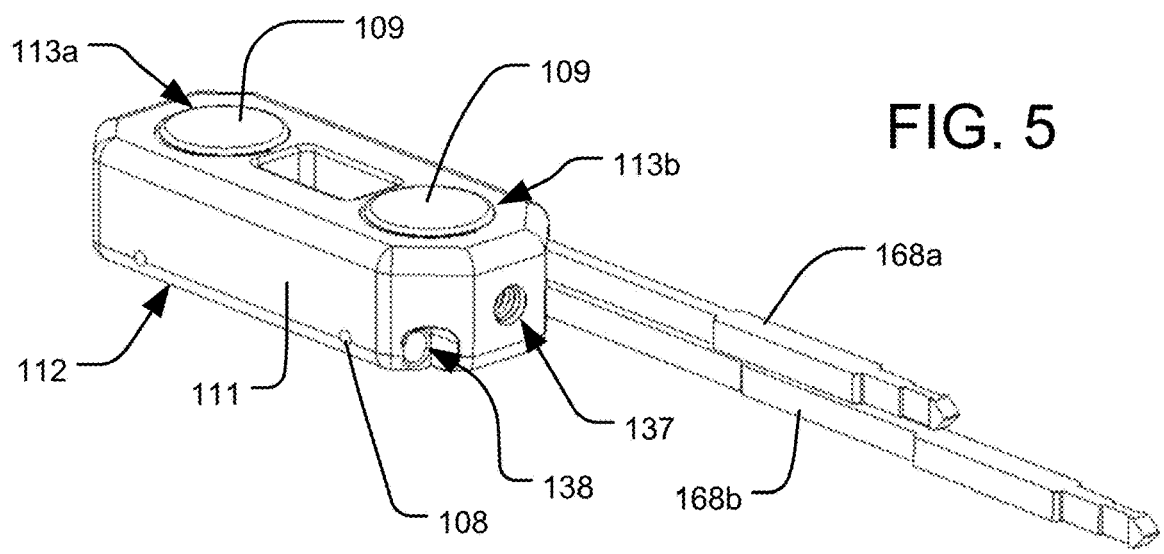
FIG. 5 is a perspective view of the spinal implant system of FIG. 4.
Figure 6:
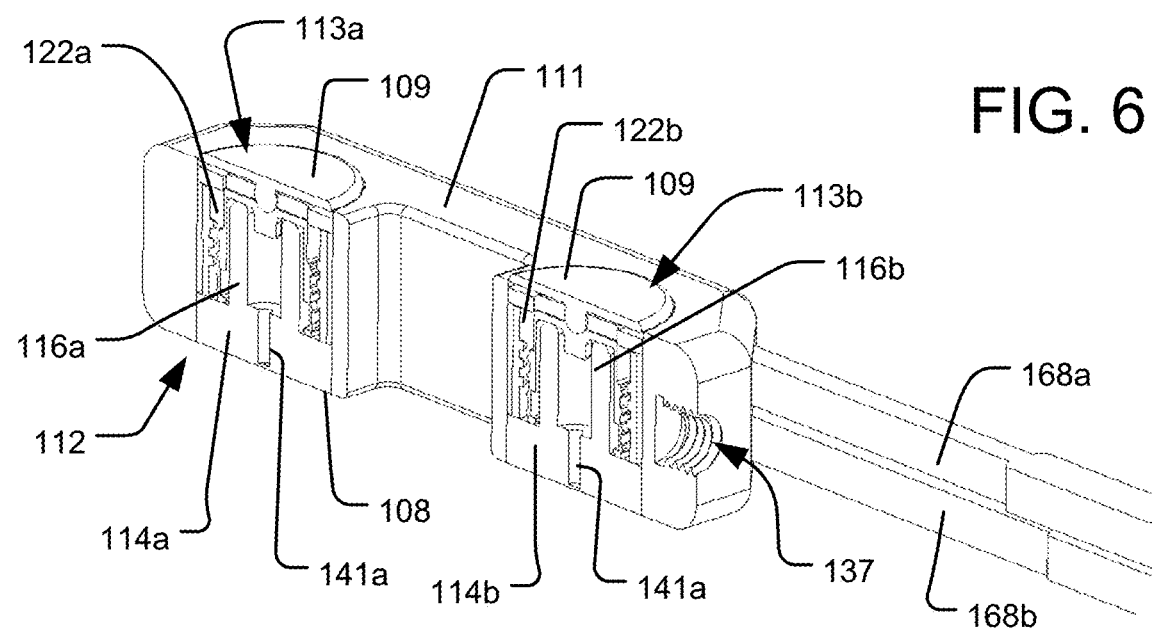
FIG. 6 is a perspective, side cross-sectional view about the longitudinal axis of the spinal implant system of FIG. 4.
Figure 7:
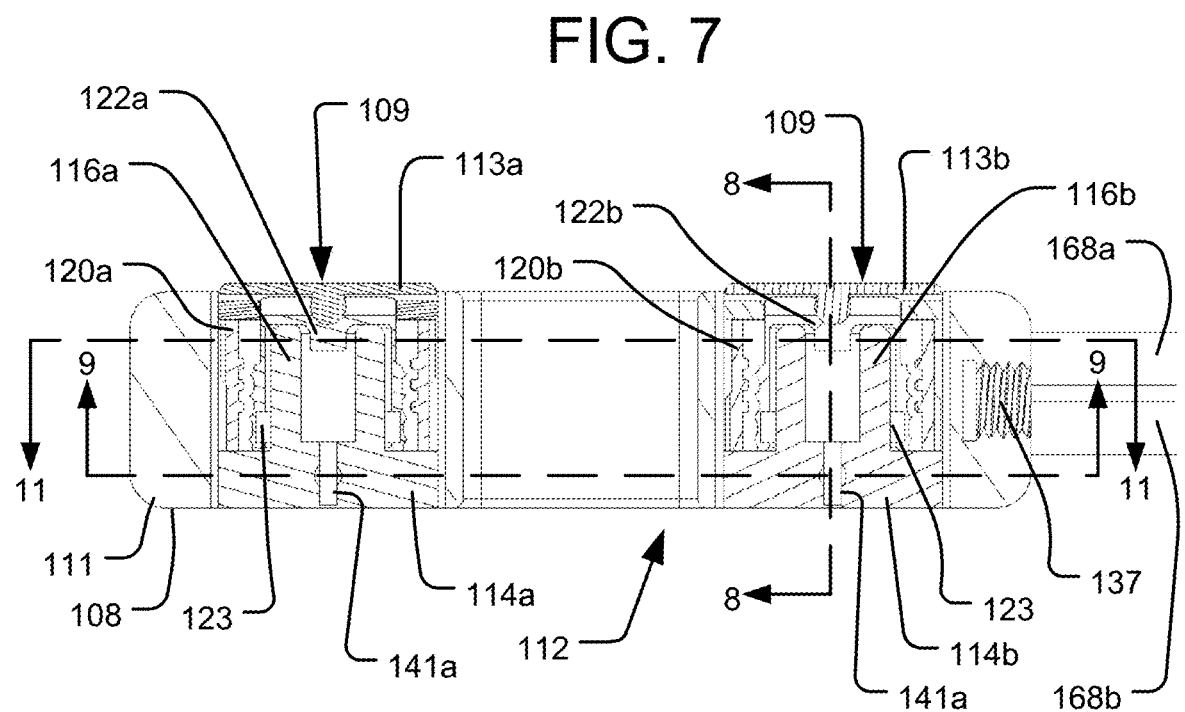
FIG. 7 is a cross-sectional side elevation view about the longitudinal axis of the spinal implant system of FIG. 4.

FIGS. 4-5 illustrate components of an intervertebral implant system 101 in accordance with another embodiment of the present invention. The system 101 includes an implant 110 having a body or housing 111 and multiple extendable support elements that are each expandable such that their top ends 105 are movable away from the housing 111. The extendable support elements may be in the form of any of the extendable support elements disclosed in the '620 Patent or the '854 Application. The extendable support elements may also be in the form of pistons 122a and 122b slidably received around associated cylindrical posts 116a, 116b affixed to the housing 111, as shown in FIGS. 4 and 6-8. For example, in the illustrated embodiment, the pistons 122a and 122b may be hollow, cylindrical structures received around associated posts 116a, 116b, which posts 116a, 116b may also be hollow, cylindrical structures having respective pressure channels 141a at their bottom ends for supplying pressurized fluid. A seal member 123, which may be in the form of an o-ring, may be positioned so as to seal the sliding interfaces between the pistons 122a, 122b and the respective posts 116a, 116b, in order to prevent the pressurized fluid from escaping through those interfaces. The pistons 122a, 122b and posts 116a, 116b may thus operate as part of a hydraulic system like that discussed in the '620 Patent and the '854 Application. In particular, when pressurized fluid is supplied to the area defined between the posts 116a, 116b and respective pistons 122a, 122b, the pressurized fluid will drive the pistons 122a, 122b to slide outward from the housing 111.

Figure 8:
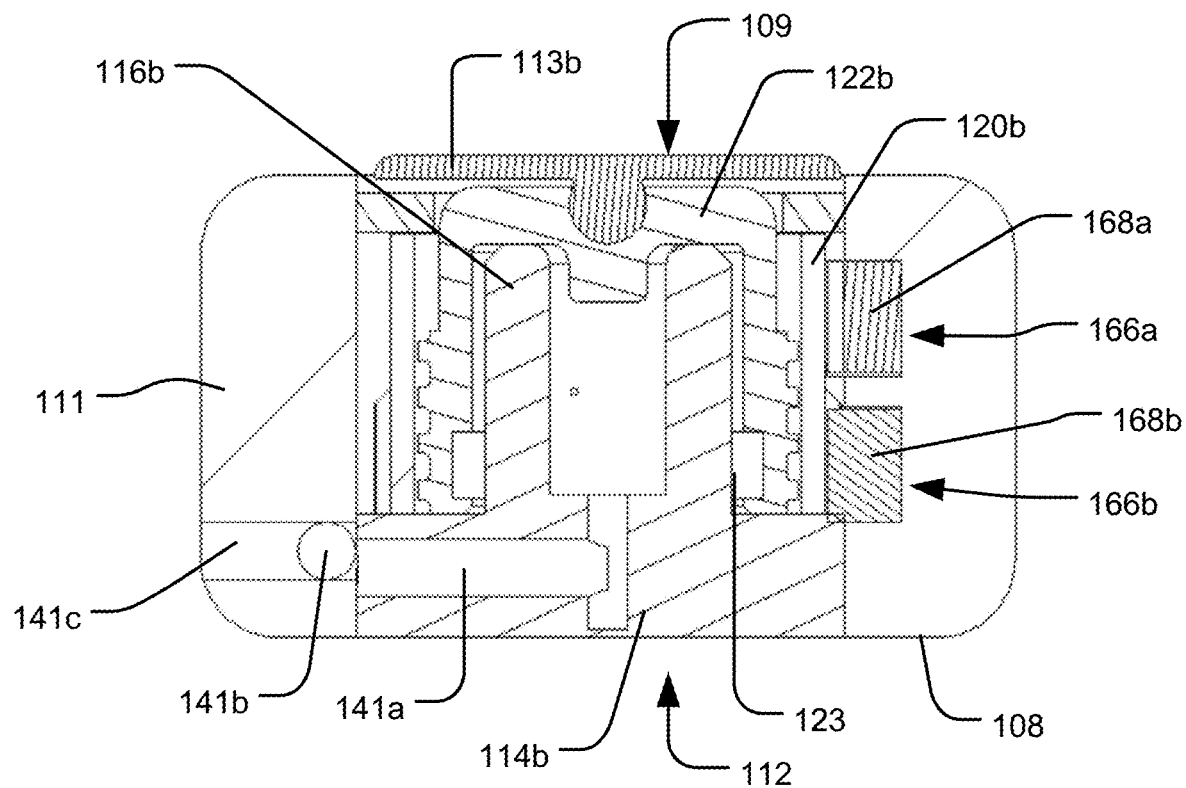
FIG. 8 is a cross-sectional rear elevation view about line 8-8 in FIG. 7.
Figure 9:
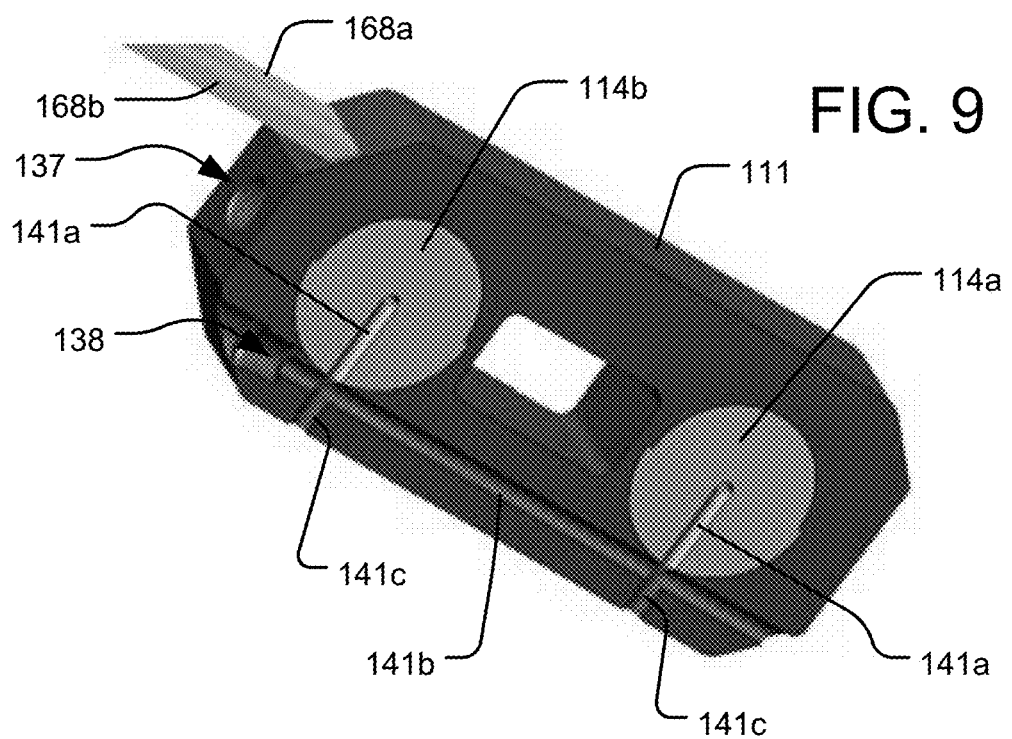
FIG. 9 is a perspective, bottom cross-sectional view of the spinal implant system of FIG. 7 about line 9-9.

As shown in FIGS. 4 and 6-9, the posts 116a, 116b may be portions of respective plug elements 114a, 114b affixed to the housing 111 by being secured within respective cylindrical bores 115a, 115b formed through the housing 111. The plug elements 114a, 114b may have wide, circular base plates 117a, 117b, which may be secured within the bottoms of the respective bores 115a, 115b. Separate alignment rings 119a, 119b may be secured (e.g., welded) within the tops of the respective bores 115a, 115b after the pistons 122a, 122b have been positioned within the bores 115a, 115b, in order to secure and align the pistons 122a, 122b within the implant. Such alignment rings 119a, 119b may have outer dimensions matching the inner dimensions of the bores 115a, 115b, and inner dimensions matching the outer profiles of the respective pistons 122a, 122b. For example, the inner profiles of the alignment rings 119a, 119b may include inwardly projecting portions or flat surfaces 124 that match recesses 146 along the outer surfaces of the pistons 122a, 122b, in order to constrain the rotational orientations of the pistons 122a, 122b. The alignment rings 119a, 119b may also act as a stop to prevent further expansion of the pistons 122a, 122b beyond a predetermined height. For example, the pistons 122a, 122b may each include at least one projecting feature that will engage the underside of the respective alignment rings 119a, 119b to prevent further expansion of the pistons. The posts 116a, 116b of the plug elements 114a, 114b may have pressure channels 141a formed therein, which communicate with a network of pressure channels 141b and 141c formed in the housing 111, as shown in FIGS. 8-9. That is, the housing 111 includes a longitudinal pressure channel 141b communicating with a pressure input port 138, into which the pressurized fluid is supplied. The network of pressure channels formed in the housing 111 may also include transverse pressure channels 141c extending from the longitudinal pressure channel 141b and communicating with the pressure channels 141a formed in the base plates 117a, 117b of the plug elements 114a, 114b. The longitudinal and transverse pressure channels 141b, 141c may be formed by drilling bores into sidewalls of the housing 111, after which plugs (not shown) may be inserted into the resulting openings formed in the sidewalls, such that the only remaining openings into the channel system are the pressure input port 138 and the exits into the pistons 122a, 122b.

Figure 10:
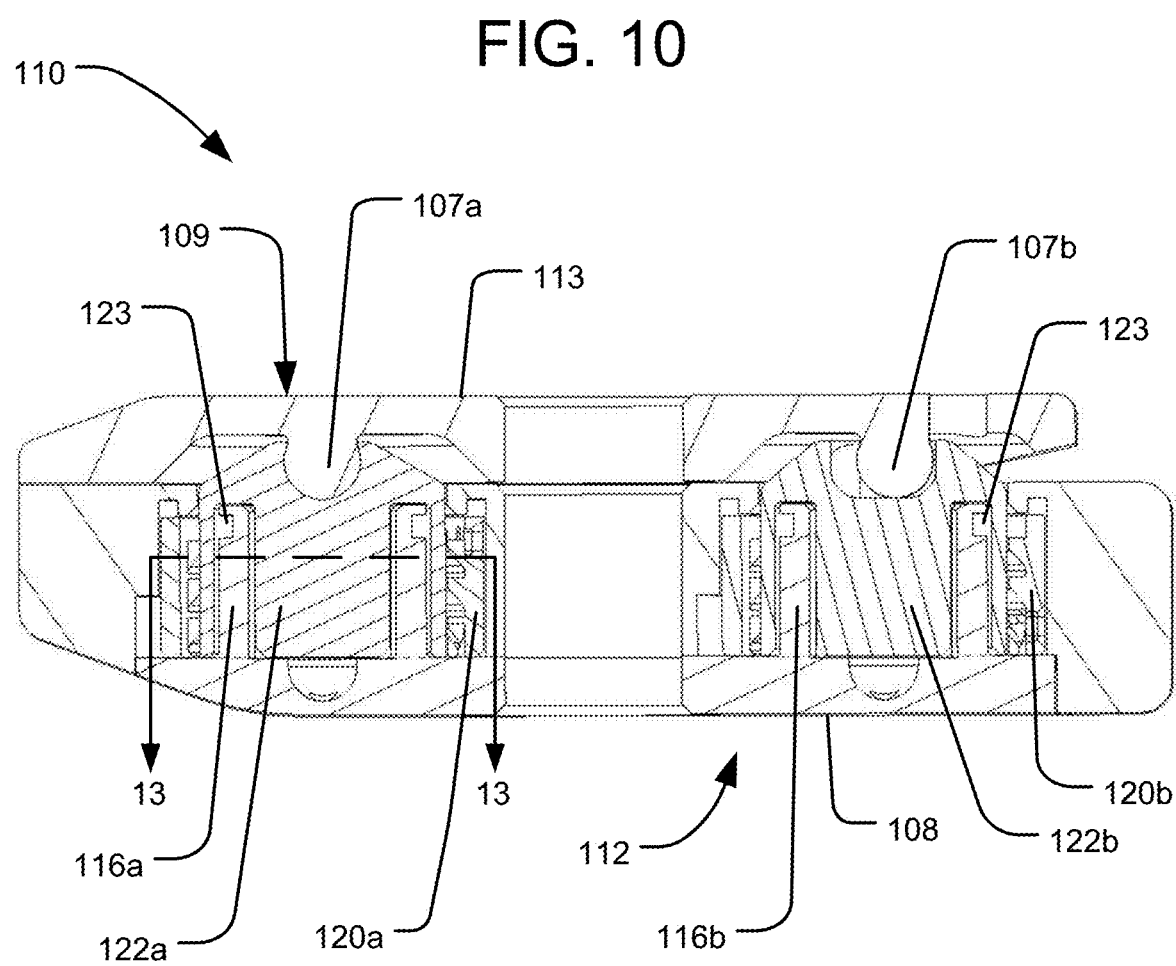
FIG. 10 is a cross-sectional side elevation view about the longitudinal axis of a variation on the embodiment of FIG. 4.

The bottom 112 of the housing 111 has a bottom end surface 108, which is a bone engaging surface for engaging a vertebra on one side (e.g., the inferior side) of the intervertebral space within which the implant 110 is positioned. The top ends 105 of the pistons 122a, 122b may represent bone engaging surfaces of the implant 110 for engaging a vertebra on the opposite side of the intervertebral space from the bottom end surface 108 (e.g., the superior side). Alternatively, the top end 105 of each piston 122a, 122b may be connected to a respective plate element 113a, 113b that has a top end surface 109 representing a bone engaging surface for engaging the vertebra on the opposite side of the intervertebral space from the bottom end surface 108, as shown in FIGS. 4-8. In yet a further alternative, both piston top ends 105 may be connected to a common top end plate 113 having a top end surface 109 representing a bone engaging surface for engaging the vertebra on the opposite side of the intervertebral space from the bottom end surface 108, as shown in FIG. 10. In such an embodiment, the top end plate 113 may be connected to each piston 122a, 122b by a pivotable connection 107a, 107b, such as a rotatable pin connection, so that the top end plate 113 can be angled with respect to each piston 122a, 122b to accommodate different amounts of translation of each piston 22a, 22b.

The implant 110 also includes a locking system having multiple locking elements 120a, 120b secured to the housing 111 and configured to lock the translational positions of the pistons 122a, 122b. The locking elements 120a, 120b may have a cylindrical shape configured to be positioned around the respective pistons 122a, 122b. The locking elements 120a, 120b may include at least one feature projecting inwardly from an inner surface thereof, and the pistons 122a, 122b may include at least one corresponding feature projecting outwardly from an outer surface thereof. Those features are configured to engage and disengage one another by rotation of the locking elements 120a, 120b with respect to the pistons 122a, 122b. For example, as shown in FIG. 4, the pistons 122a, 122b may each include a series of spaced apart ribs 118 projecting from their outer surfaces, and the inner surfaces of the locking elements 120a, 120b may each include a series of spaced apart ribs 121. In particular rotational orientations of each locking element 120a, 120b (referred to as a "locked configuration"), the ribs 121 of the locking element 120a, 120b mesh with the ribs 118 of the associated piston 122a, 122b, thus preventing expansion the piston 122a, 122b. The ribs 121 of the locking elements 120a, 120b may be structured and arranged to align and fit within the recesses 146 along the outer surfaces of the pistons 122a, 122b at particular rotational positions of each locking element 120a, 120b (referred to as an "unlocked configuration"). In the unlocked configuration, there is clearance between the ribs 118 of a piston 122a, 122b and the ribs 121 of the associated locking element 120a, 120b, thus leaving the pistons 122a, 122b free to translate outwardly under the influence of the pressurized fluid, or free to translate back inwardly so as to collapse the implant if the fluid is depressurized or withdrawn.

Figure 11:
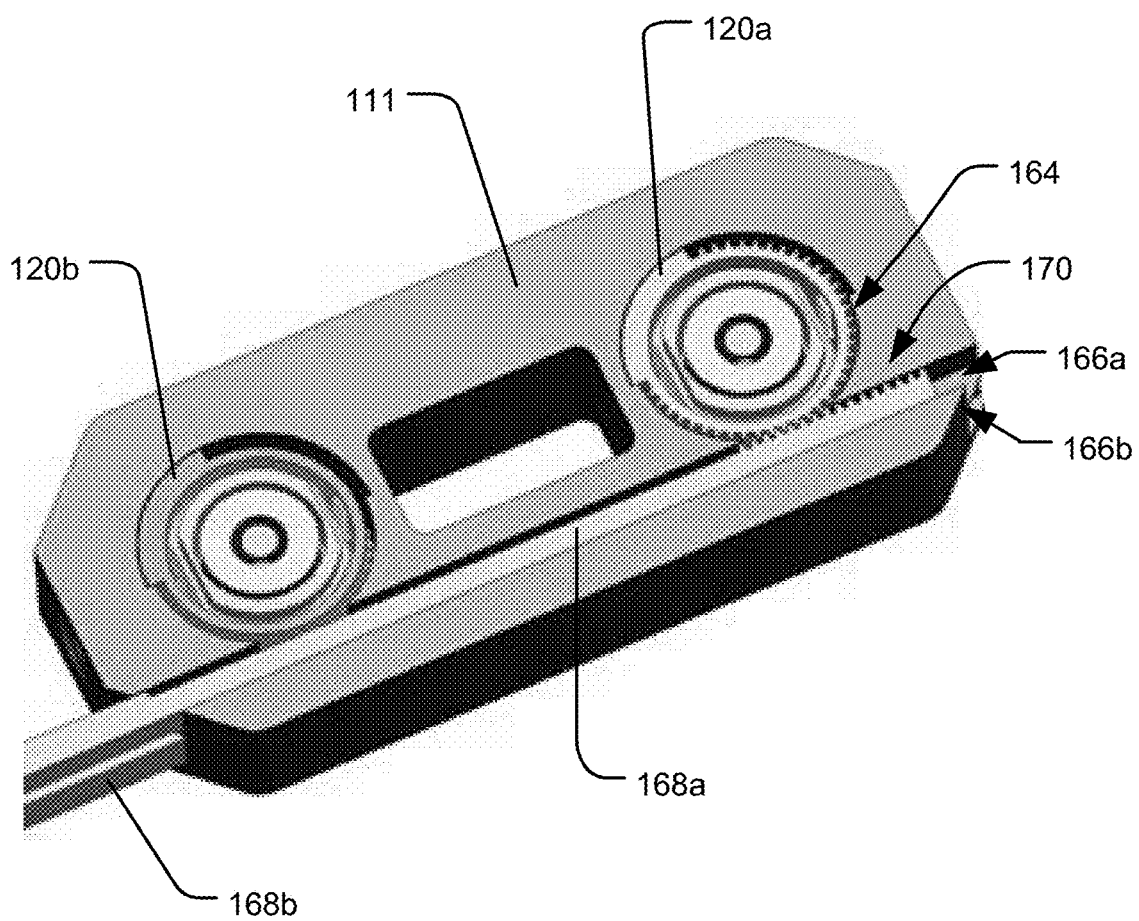
FIG. 11 is a perspective, top cross-sectional view of the spinal implant system of FIG. 7 about line 11-11.
Figure 12A:
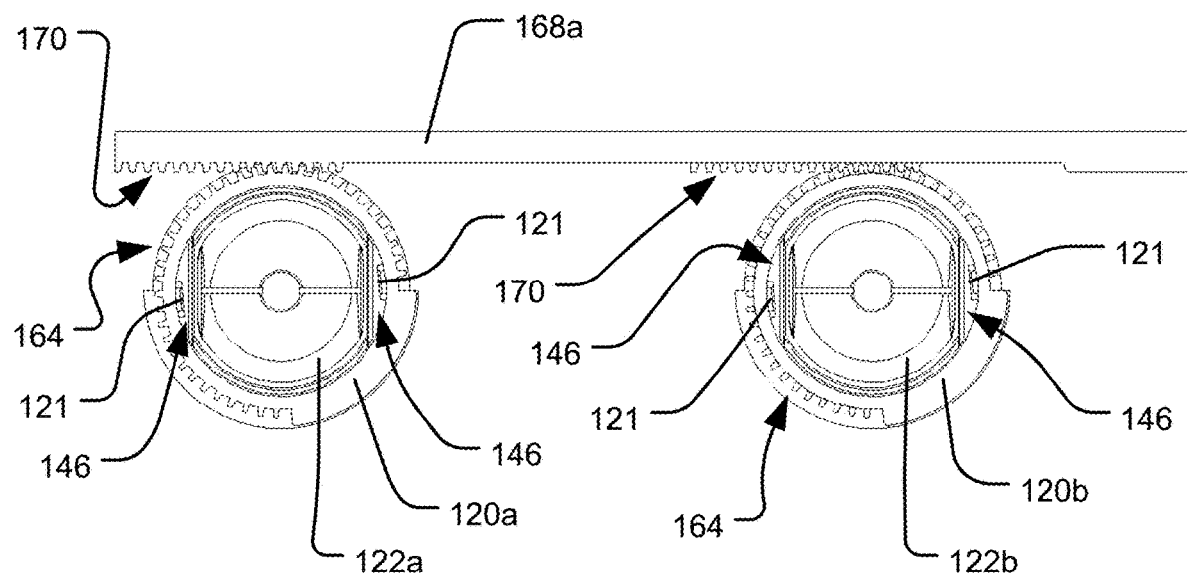
FIGS. 12A-B are plan views of locking components of the embodiment of FIG. 4 in different configurations.

A rack-and-pinion arrangement may be used to control the rotational positions of the locking elements 120a, 120b, and thus the locked and unlocked status of the associated pistons 122a, 122b, as shown in FIG. 11. For example, each locking element 120a, 120b may include a plurality of teeth 164 on the outer surface thereof, in order to engage teeth 170 of a corresponding control rod 168a, 168b, such that the rotational position of each locking element 120a, 120b may be controlled by the linear position of the control rod 168a, 168b within a channel 166a, 166b in the implant housing 111. As shown in FIG. 12A, in which the control rods 168a, 168b are advanced to a distal-most position, the locking elements 120a, 120b are in an unlocked configuration, such that the ribs 121 of the locking elements 120a, 120b are aligned with the recesses 146 of the pistons 122a, 122b, and thus the pistons 122a, 122b are free to translate outwardly. By retracting the control rods 168a, 168b proximally, as shown in FIG. 12B, the locking elements 120a, 120b are moved to a locked configuration, such that the ribs 121 of the locking elements 120a, 120b are rotated into engagement with the ribs 118 of the pistons 122a, 122b, thus preventing the pistons 122a, 122b from translating outwardly.

Figure 12B:
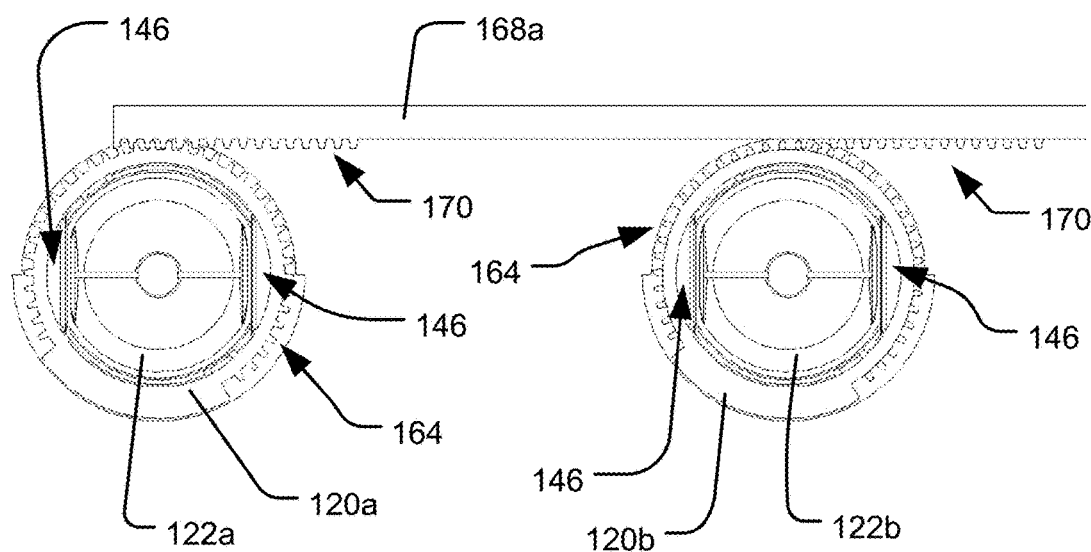
Figure 13A:
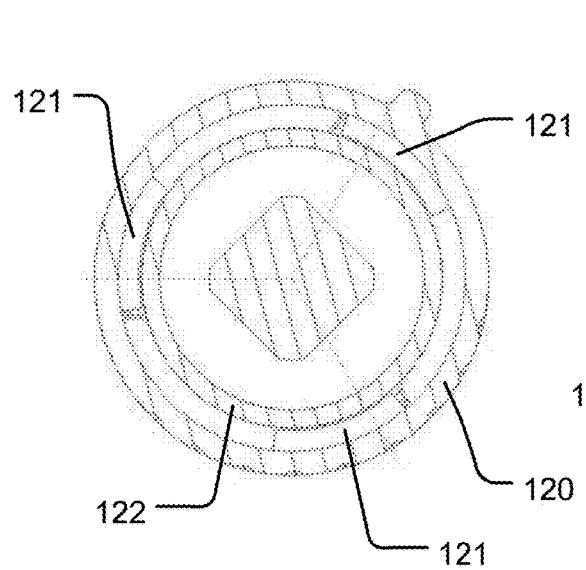
FIG. 13A is a cross-sectional plan view about line 13-13 of the alternative locking component illustrated in FIG. 10 in a locked configuration.
Figure 13C:
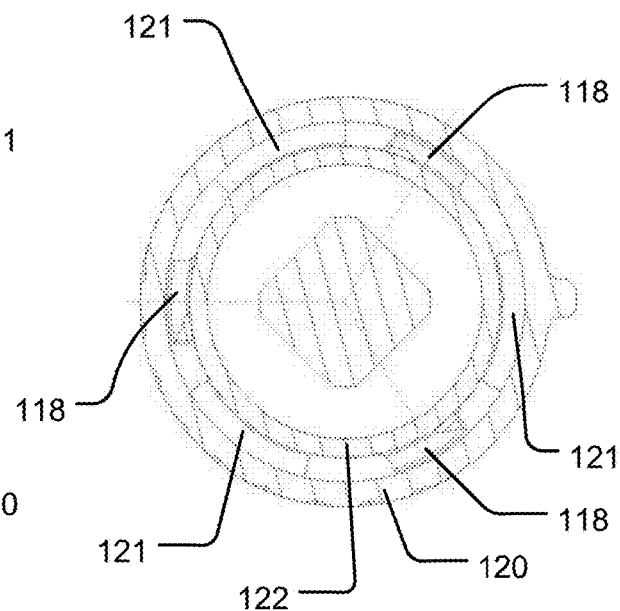
FIG. 13C is a cross-sectional plan view about line 13-13 of the alternative locking component illustrated in FIG. 10 in an unlocked configuration.
Figure 13B:
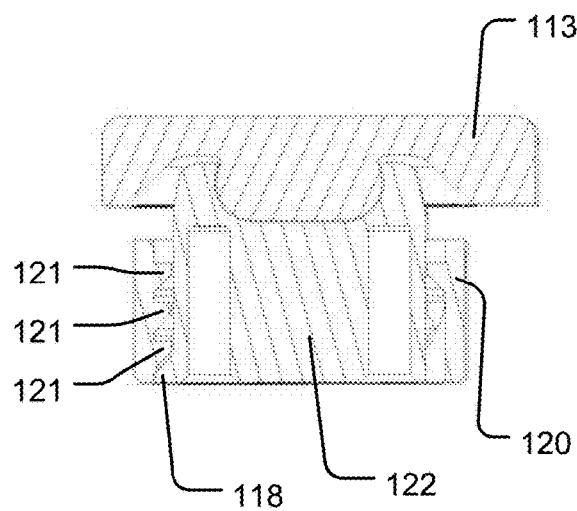
FIG. 13B is a side, cross-sectional view about the implant's longitudinal axis of the locking component of FIG. 13A in a locked configuration.
Figure 13D:
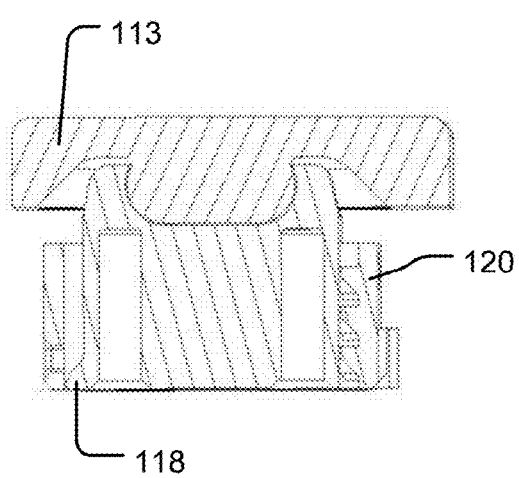
FIG. 13D is a side, cross-sectional view about the implant's longitudinal axis of the locking component of FIG. 13A in an unlocked configuration.

In the arrangement of FIGS. 12A-B, each piston 122a, 122b includes two, diametrically opposed recesses 146, and the locking elements 120a, 120b each include two corresponding sets of ribs 121. In an alternative arrangement, rather than a series of spaced apart ribs 118, only a single rib 118 may be provided on each piston 122a, 122b. That single rib 118 may be discontinuous in particular circumferential regions with which the ribs 121 of the locking elements 120a, 120b align in the unlocked configuration, so that there is clearance for the pistons 122a, 122b to translate. As shown in FIGS. 13A-D, which are views of such an alternative arrangement as incorporated into the embodiment of the implant 110 of FIG. 10, the pistons 122a, 122b may include three such discontinuous regions, although more or fewer discontinuous regions are also within the scope of the present invention. As illustrated in the locked configuration shown in FIGS. 13A-B, the ribs 121 of the locking element 120 are rotationally aligned with the solid portions of the rib 118 of the piston 122, and thus the piston 122 is prevented from translating outwardly. As for the unlocked configuration illustrated in FIGS. 13C-D, the ribs 121 of the locking element 120 have rotated into alignment with the discontinuous regions of the rib 118 of the piston 122, such that the piston 122 is free to translate outwardly. The reverse arrangement (not shown) is also within the scope of the present invention. That is, instead of a series of spaced apart ribs 121 on the locking elements 120*a*, 120*b*, only a single rib 121 having discontinuous regions may be provided on the inner surface of each locking element 120*a*, 120*b*. Thus, in order to lock one of the pistons 122*a*, 12*b* at its current level of displacement, the rib 121 of one of the locking elements 120*a*, 120*b* may be rotated into engagement with whichever rib 118 of the associated piston 122*a*, 122*b* is at that level.

By manipulating the control rods, and thus the locked and unlocked configurations of the pistons, as discussed above, the expansion of the different pistons can be individually controlled while applying a single fluid pressure to all the pistons. For example, by applying a pressure to the pressure channels sufficient to expand all of the pistons, any one or more of the pistons can be selectively locked by appropriate manipulation of the position of the associated control rod, such that the remaining unlocked pistons continue to translate outward from the implant housing.

Figure 14:
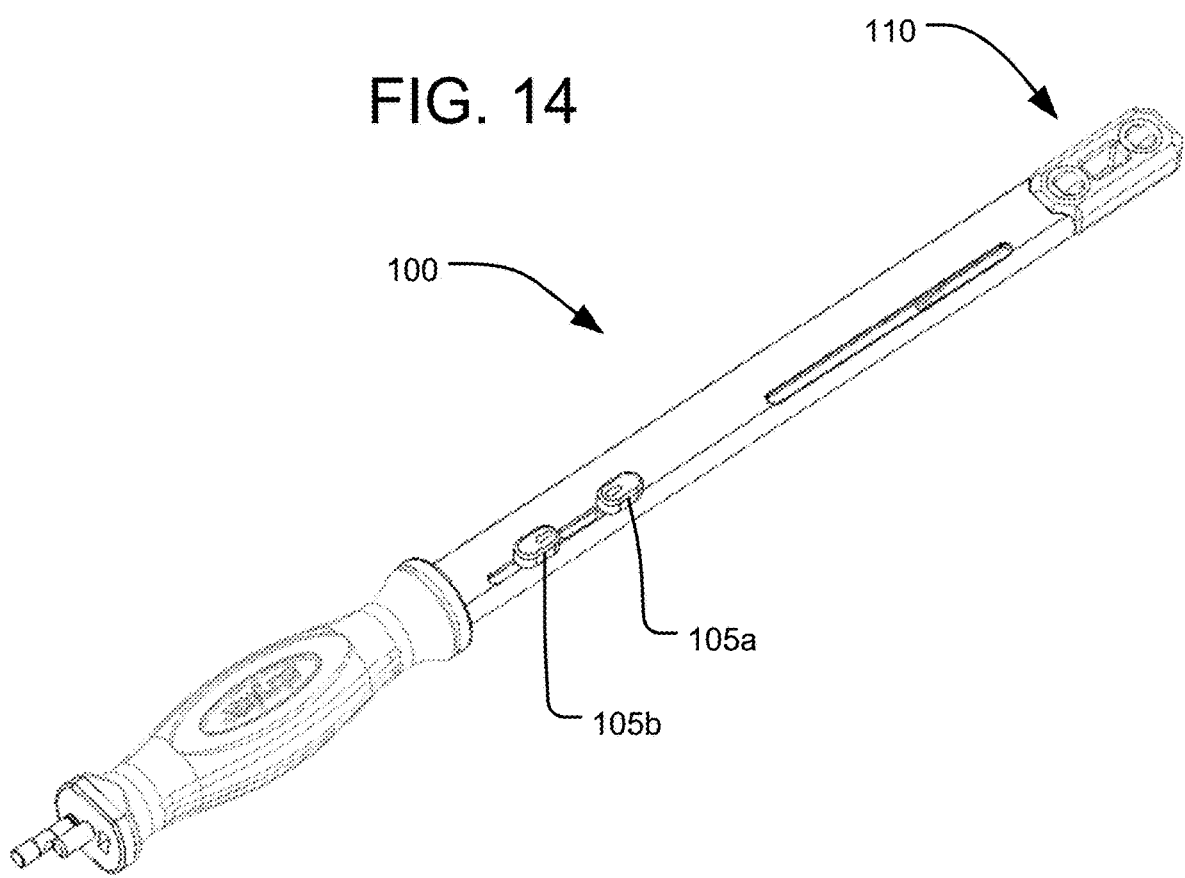
FIG. 14 is a perspective view of the spinal implant system of FIG. 4 including a delivery tool.

In order to control the translational position of the control rods 168*a*, 168*b*, a delivery tool 100 for inserting and positioning the implant 110 within the intervertebral space may include respective sliders 105*a*, 105*b* linearly movable by a user along at least a portion of the delivery tool 100, as shown in FIG. 14. The delivery tool 100 may be securely attached to the proximal end of the implant 110 by a delivery tool anchor 137 (see FIGS. 4-7), which may include a threaded bore formed in the implant 110. In addition, the delivery tool 100 may include a conduit for communicating with the pressure input port 138, in order to supply the pressurized fluid to the implant 110. The delivery tool anchor 137 having a threaded bore for secure attachment to the delivery tool 100 need not be a separate opening in the implant 110 from the pressure input port 139 for supplying pressurized fluid, and both functions can be performed by a common opening, as shown in the embodiment of FIGS. 16-19. The locking elements 120*a*, 120*b* are desirably configured such that fully retracting the associated control rods 168*a*, 168*b* from the implant 110, such as when the delivery tool 100 is disconnected and removed from the patient's body, will leave the locking elements 120*a*, 120*b* in a locked configuration.

Figure 15:
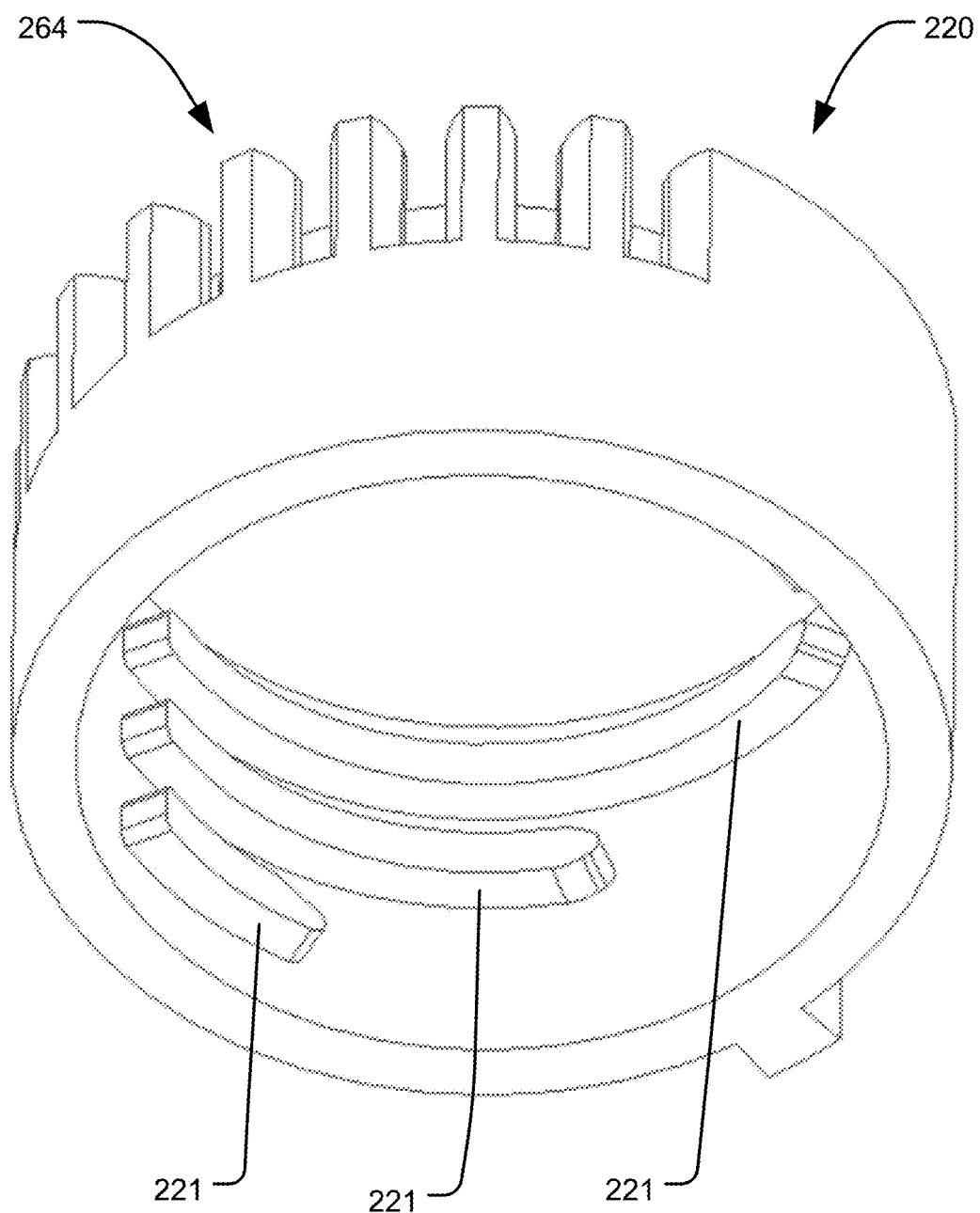
FIG. 15 is a perspective view of a locking element in accordance with another embodiment of the invention.

A further alternative embodiment in accordance with the present invention includes rotatable locking elements 220 similar to those of the embodiment of FIGS. 4-13D, except that the locking elements 220 are configured to selectively define a maximum amount of permitted movement of the associated piston 222, rather than locking the position of the associated piston 222. For example, as shown in FIG. 15, the inner surface of the locking element 220 includes a series of spaced apart ribs 221, where each successive rib 221 extends to a different, increasing circumferential position along the inner surface of the locking element 220. Moreover, the associated piston 222 may include a pin 218 projecting from its outer surface. Thus, each locking element 220 can be rotated to a desired position so as to define a maximum amount of expansion of the associated piston 222, by aligning the rib 221 corresponding to the desired height such that it is vertically above the pin 218. In that manner, expansion of the piston 222 by the pressurized fluid will cause the piston to translate until it engages and stops at the aligned rib 221. The height of the piston 222 may then be locked at that position by fully retracting the associated control rod 268, thus rotating the locking element 220 until the pin 218 is constrained between two adjacent ribs 221.

Each locking element 220 and piston 222 combination need not have only one pin 218 and one corresponding series of ribs 221, however. In alternative embodiments, multiple pins 218, each with a corresponding series of ribs 221, may be equally spaced apart about the circumference of the piston 218 and locking element 220. For example, the embodiment illustrated in FIGS. 16-17 has three pins 218 equally spaced about the circumference of each piston 222.

Figure 19:
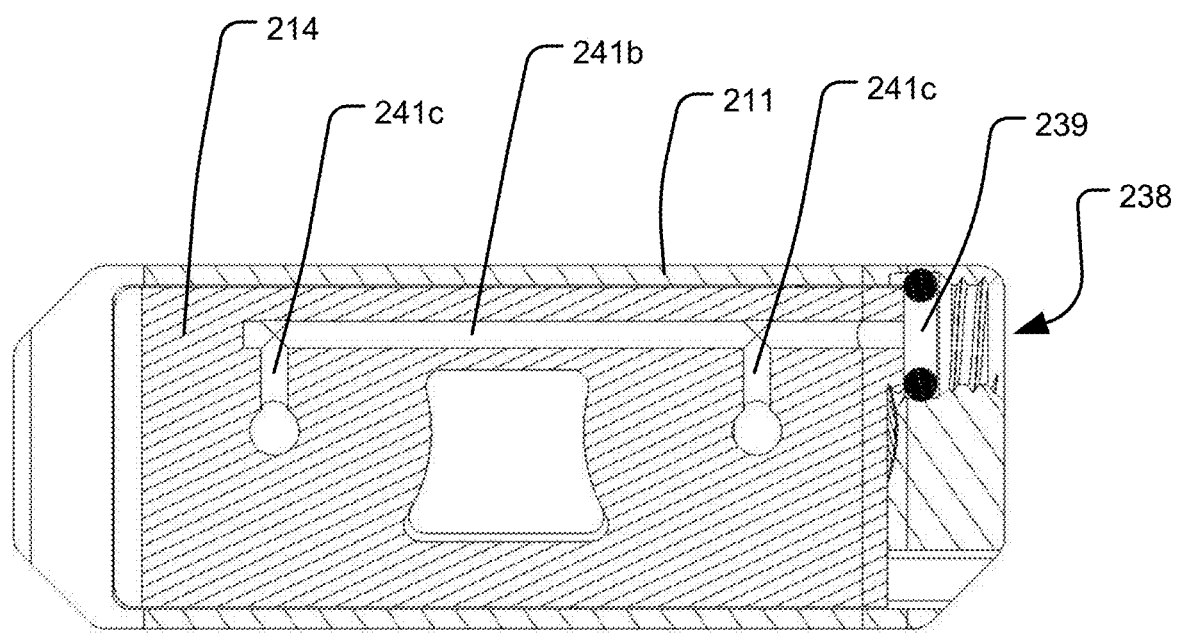
FIG. 19 is a bottom cross-sectional view about line 19-19 of the spinal implant system of FIG. 16B.

FIGS. 16-19, in which reference numerals like those in earlier embodiments refer to analogous elements (and therefore not all numbered elements will be separately discussed again), illustrate an embodiment of an implant 210 having distal and proximal locking elements 220*a*, 220*b* like that shown in FIG. 15. Thus, in such an embodiment, the locking elements 220*a*, 220*b* may be individually controlled by respective control rods 268*a*, 268*b* so that the associated pistons 222*a*, 222*b* can be expanded to different desired heights, and the bone engaging component(s) (e.g., top end plate 213) can thus be translated and angled, as with the previously-discussed embodiments. Many of the other structures of the embodiment of FIGS. 16-19 are substantially the same as those of the embodiment of FIGS. 4-13D, except that, instead of the posts 116*a*, 116*b* along which the pistons 122*a*, 122*b* slide being portions of respective plug elements 114*a*, 114*b*, the posts 216*a*, 216*b* of the embodiment of FIGS. 16-19 may be portions of a single bottom plate element 214. As shown in FIG. 19, that plate element 214 may include a network of longitudinal and transverse pressure channels 241*b*, 241*c* similar to those of the embodiment of FIGS. 4-13D, such that the network of channels communicates the pressurized fluid from a pressure input port 238 to the pistons 222*a*, 222*b*. The pressure input port 238 may include a threaded section for secure attachment to a delivery tool for delivering the implant 210, such that the pressure input port 238 also functions like the delivery tool anchor 137 discussed above. A sealing member, such as o-ring 239, may also be provided within the pressure input port 238, so as to seal the fluid connection between the pressure input port 238 and the delivery tool.

Figure 16A:
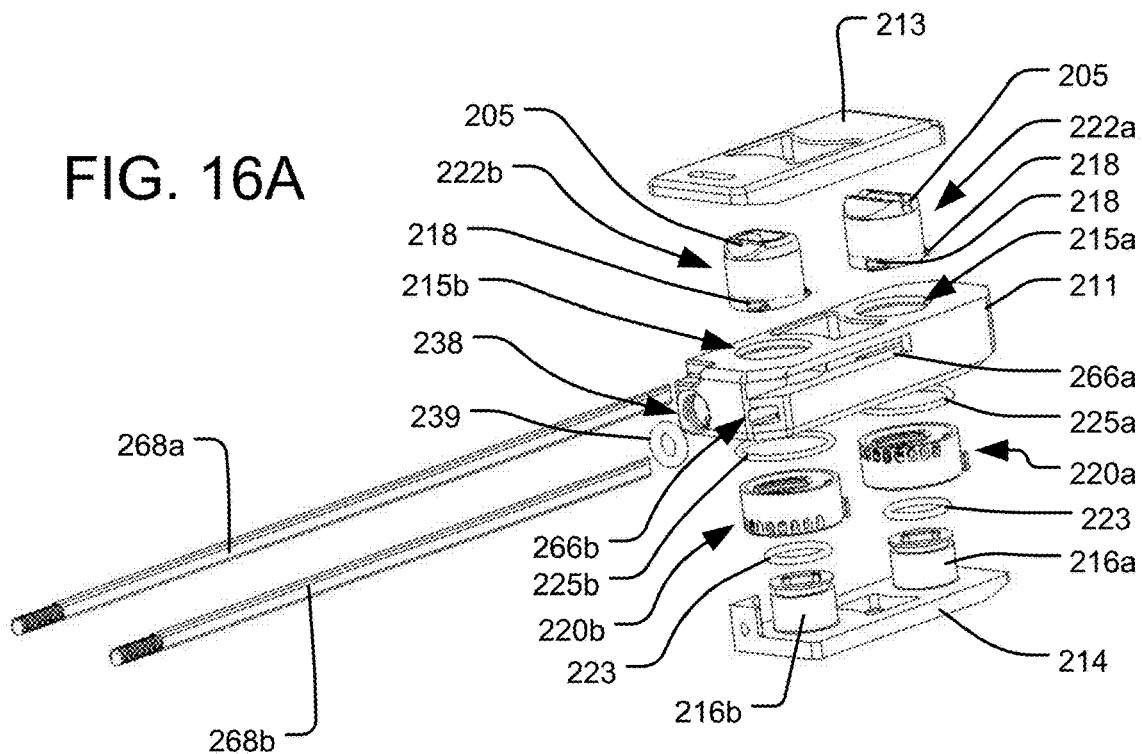
FIGS. 16A-B are exploded, perspective views (taken from different angles) of a spinal implant system in accordance with an embodiment of the invention including the locking element of FIG. 15.
Figure 16B:
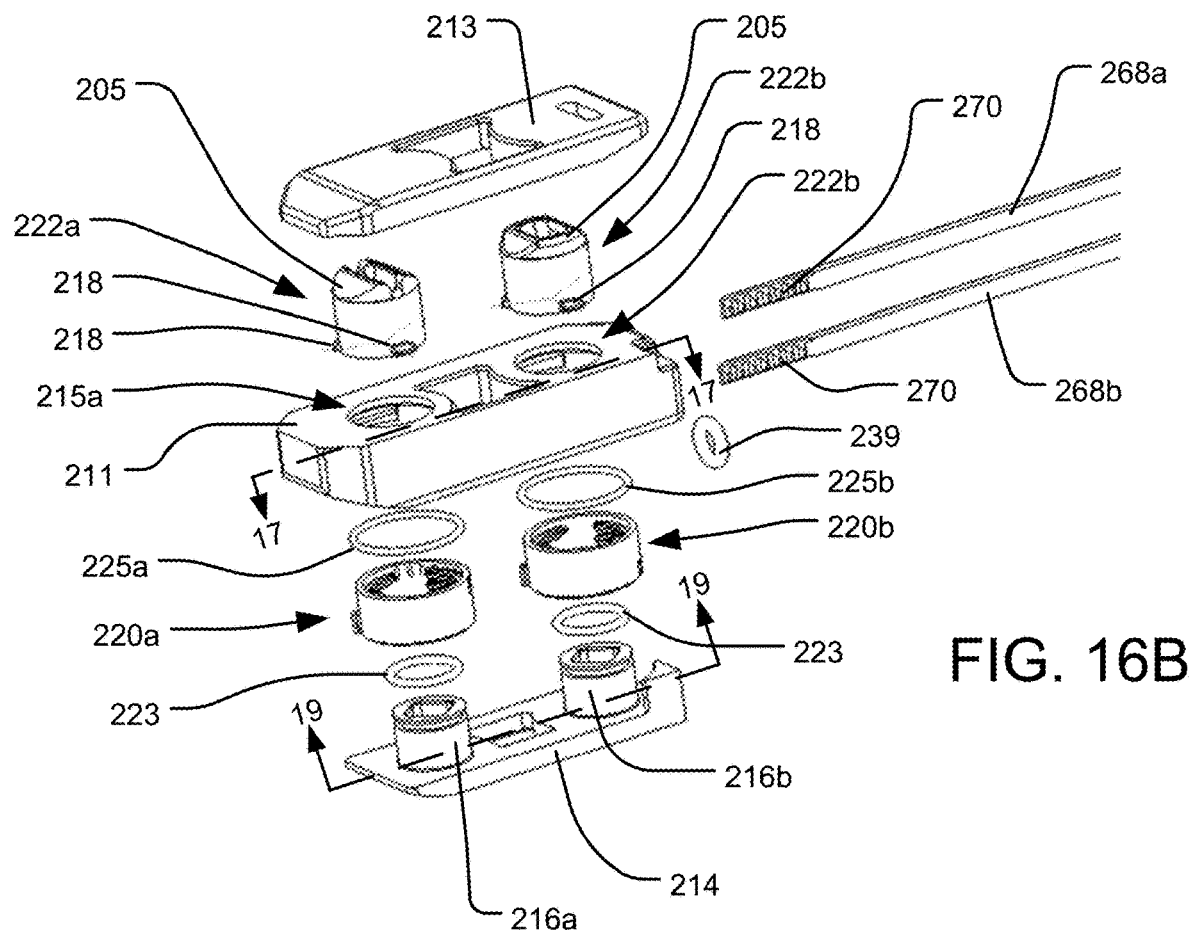
Figure 17:
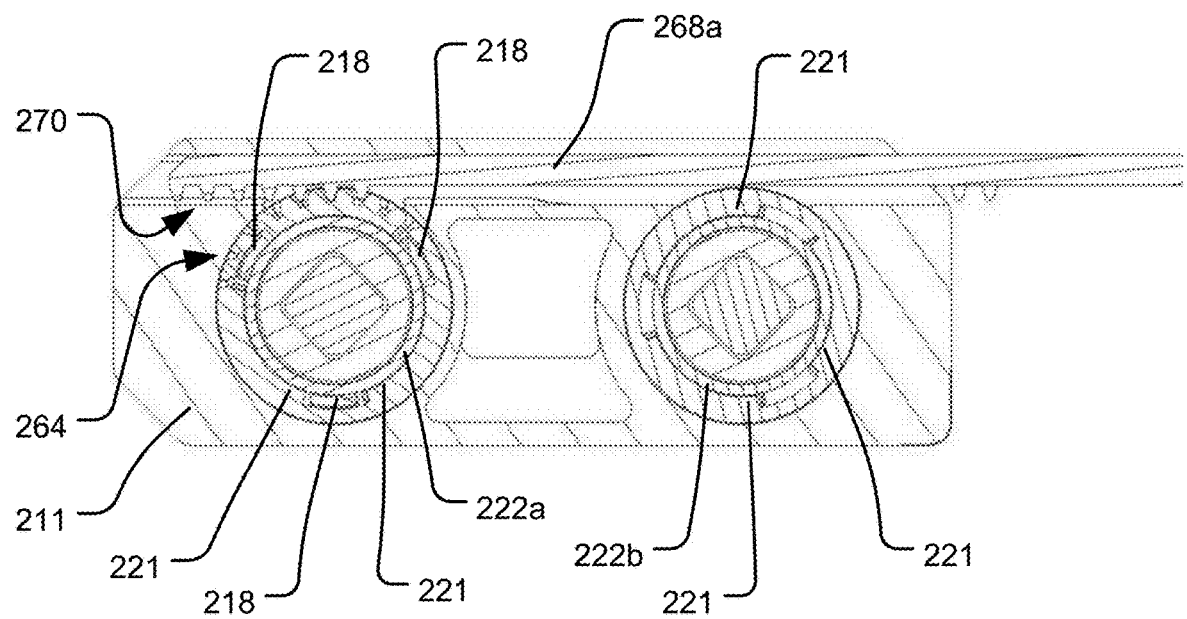
FIG. 17 is a cross-sectional plan view about line 17-17 of the spinal implant system of FIG. 16B.
Figure 18:
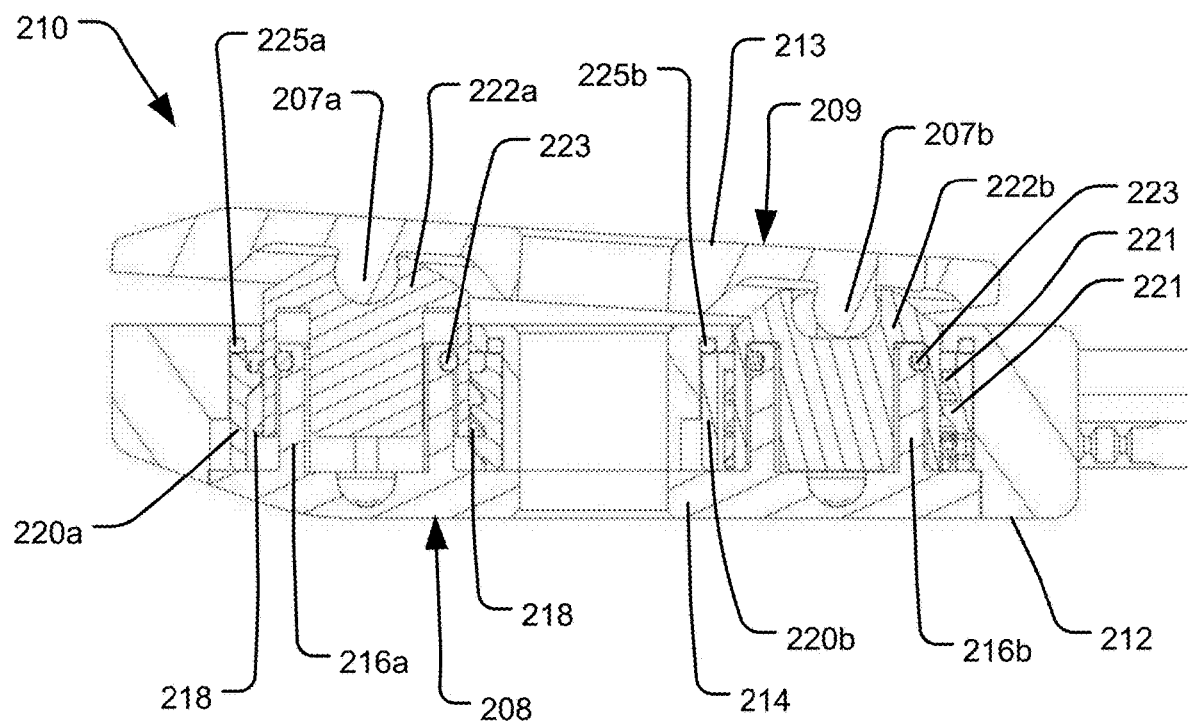
FIG. 18 is a cross-sectional side elevation view about the longitudinal axis of the spinal implant system of FIG. 17.

Other differences between the embodiment of FIGS. 16-19 and the embodiment of FIGS. 4-13 include the fact that the embodiment of FIGS. 16-19 does not have separate alignment rings like those illustrated in FIGS. 16A-B. Instead, similarly shaped alignment components may be integrally formed with the housing 211 of the implant 210, or the bores 215*a*, 215*b* through the housing 211 may be shaped to constrain the rotational orientations of the pistons 222*a*, 222*b*. Also, as shown in FIG. 16A, the channel 266*a* for the control rod 268*a* that controls the distal locking element 220*a* opens outwardly through a side wall of the housing 211 along a portion of the longitudinal extent of the housing 211. Such extended opening into the channel 266*a* through the side wall, which may beneficially allow for more clearance between the control rod 268*a* and the proximal locking element 220*b* that it bypasses, may also be included in the embodiment of FIGS. 4-13, although not shown in those figures. The embodiment of FIGS. 16-19 also includes friction rings 225*a*, 225*b* compressed between the tops of the locking elements 220*a*, 220*b* and the underside of the top of the housing 221 in the assembled configuration. The friction rings 225*a*, 225*b* may be made out of rubber or a polymeric material that has a relatively high coefficient of friction, so that there is enough resistance to rotation of the locking elements 220*a*, 220*b* that their rotational positions are maintained when not intentionally rotated by the user using the control rods 268a, 268b. Such friction rings, although not shown in FIGS. 4-13, can also be used in the embodiment of those figures.

The above-described embodiments illustrated in FIGS. 4-19 are desirably structured to be used in a PLIF technique. That is, the generally linear shape of each of the implants 110, 210 between the distal and proximal ends of the implant may be particularly suitable for inserting two such implants 110, 210 into an intervertebral space (one on either side of the spine) along a posterior to anterior direction, such that the distal end of the implant is positioned more anteriorly with respect to the spine than the more posteriorly positioned proximal end of the implant. However, the same operative components discussed above can also be included in implants structured to be used in a TLIF technique or along a lateral approach. For example, an implant structured to be used in a lateral approach may have a similar configuration to one of those discussed above, but may be sized to cover a substantial portion of the disc space. As for an implant structured to be used in a TLIF technique, the same operative components discussed above can be incorporated into an implant having an overall kidney bean-like shape. In such an embodiment, the channels for receiving the control rods may be linear between the locking elements, as shown in the above-discussed figures, or the channels may follow an arcuate path. If the channels are arcuate, the control rods may have a corresponding arcuate shape or may be flexible to conform to the paths of the channels.

Figure 20:
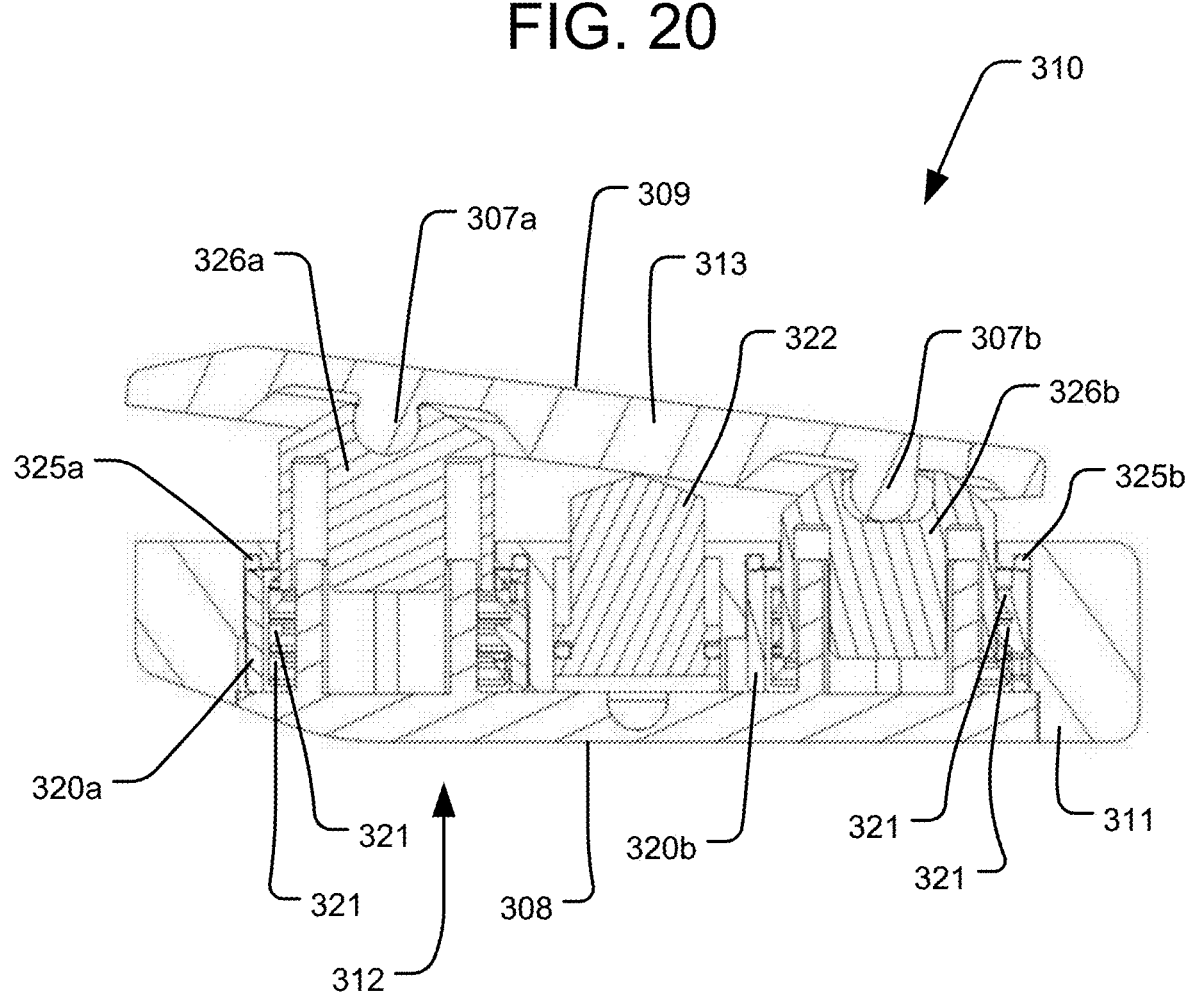
FIG. 20 is a cross-sectional side elevation view about the longitudinal axis of a spinal implant system in accordance with another embodiment of the present invention.

Although the locking elements in the embodiments of FIGS. 4-19 are structured to surround the associated pistons, alternative embodiments in accordance with the present invention need not be arranged in that manner. For example, in another embodiment of the invention illustrated in FIG. 20, a single extendable support element, which may include a translating piston 322 driven by a pressurized fluid, may be provided between a housing 311 of the implant 310 and a top end plate 313. Reference numerals in FIG. 20 that are like those in earlier embodiments refer to analogous elements, and therefore not all numbered elements will be separately discussed again. The implant of FIG. 20 may include two or more locking elements 320 similar to those discussed above at different locations across the implant 310, in order to individually control the amount of expansion of the top plate 313 at the location of each locking element 320. For example, the implant 310 may include a distal locking element 320a and a proximal locking element 320b, with the extendable support element (e.g., piston 322) being centrally located therebetween. In operation, the extendable support element may be actuated to drive the movement of the top end plate 313 away from the housing of the implant, and each locking element 320a, 320b can be individually manipulated to control the amount of expansion of the top end plate 313 at the distal and proximal ends. Rather than engaging extendable support elements positioned therein, the locking elements 320a, 320b may each be configured to lock the expanded position of the top end plate 313 at the location of the locking element by lockingly engaging a structure connected to the top end plate 313. For example, the top end plate 313 may include downwardly extending shafts 326a, 326b coupled thereto, which shafts have outer surfaces with similar configurations to the pistons described above (i.e., each having a series of spaced apart ribs projecting from the outer surface), where the shafts 326a, 326b are received within open interior regions of the respective locking elements 320a, 320b and are lockingly engageable by the locking elements in similar ways to those described above (e.g., by rotational engagement with inwardly projecting ribs 321 of the locking elements). The top end plate 313 may be indirectly coupled to the housing 311 (e.g., via the extendable support element and/or locking elements) by pivotable connections, so that the top end plate 313 can achieve angled orientations with respect to the housing 311 and so that the top end plate 313 can continue to translate at the location of a locking element 320 that is in an unlocked configuration, even when the other locking element is in a locked configuration. For example, as shown in FIG. 20, the shafts 326a, 326b may be coupled to the top end plate 313 by respective pivotable connections 307a, 307b, such as rotatable pin connections, and the piston 322 may contact the plate 313 in such a way that the contact point can slide along the plate, so as to not over-constrain the top end plate 313.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant system, comprising:
a spinal implant for placement between first and second vertebral bodies, the spinal implant including:
  a body having a first surface for engaging a first vertebral body;
  a first extendable support element connected to the body at a first location, the first extendable support element being configured to expand such that a first end of the first extendable support element moves away from the body; and
  a second extendable support element connected to the body at a second location, the second extendable support element being configured to expand such that a second end of the second extendable support element moves away from the body; and
a tool selectively positionable with respect to the spinal implant so as to independently or simultaneously expand the first and second extendable support elements,
  wherein when the tool is in a first position with respect to the spinal implant the first and second extendable support elements independently expand, and
  wherein when the tool is in a second position with respect to the spinal implant the first and second extendable support elements simultaneously expand.

2. The spinal implant system of claim 1, wherein the spinal implant is configured to allow the tool to move within the spinal implant to expand the first and second extendable support elements.

3. The spinal implant system of claim 2, wherein the spinal implant is configured to allow longitudinal movement of the tool within the spinal implant to expand the first and second extendable support elements.

4. The spinal implant system of claim 3, wherein the spinal implant includes a channel extending between the first and second extendable support elements, such that the longitudinal movement of the tool is within the channel.

5. The spinal implant system of claim 1, wherein each of the first and second extendable support elements includes a piston slidably received within a cylinder.

6. The spinal implant system of claim 5, wherein the first and second extendable support elements are configured to be extended by a fluid.

7. The spinal implant system of claim 6, wherein the spinal implant includes a channel extending between the first and second extendable support elements.

8. The spinal implant system of claim 7, wherein the tool supplies the fluid to the first and second extendable support elements, and wherein the channel of the spinal implant is configured to allow the tool to move therealong to selectively supply the fluid to the first and second extendable support elements.

9. The spinal implant system of claim 7, wherein the tool includes an internal fluid passageway.

10. The spinal implant system of claim 9, wherein, the channel of the spinal implant is adapted to receive the tool therein, and wherein, when the tool is received within the channel, an exterior fluid passageway is defined between an inner surface of the channel and an exterior surface of the tool, the exterior fluid passageway communicating with the internal fluid passageway via at least one exit port of the tool.

11. The spinal implant system of claim 10, wherein the tool is longitudinally movable along the channel, such that the exterior fluid passageway can be moved to selectively communicate with either or both of the first and second extendable support elements.

12. The spinal implant system of claim 10, wherein the exterior fluid passageway is defined between a first seal member and a second seal member spaced apart along a length of the tool, the first and second seal members being configured to sealingly engage the inner surface of the channel.

13. The spinal implant system of claim 10, wherein the exterior fluid passageway is at least partially defined by a recessed portion of the exterior surface of the tool.

14. The spinal implant of claim 1, wherein the first end of the first extendable support element and the second end of the second extendable support element are connected by a plate having a second surface for engaging a second vertebral body.

15. The spinal implant of claim 14, wherein the first end of the first extendable support element is connected to the plate by a first pivotable connection and the second end of the second extendable support element is connected to the plate by a second pivotable connection.

16. A system, comprising:
an implant for placement between first and second vertebral bodies, comprising:
a body having a first surface for engaging a first vertebral body;
a first extendable support element connected to the body and having a first end movable away from the body at a first location, the first extendable support element being operable between an activated control state, in which the first extendable support element is actuatable to expand so as to induce movement of the first end away from the body, and a deactivated control state, in which the first extendable support element is not actuatable to expand;
a second extendable support element connected to the body and having a second end movable away from the body at a second location, the second extendable support element being operable between an activated control state, in which the second extendable support element is actuatable to expand so as to induce movement of the second end away from the body, and a deactivated control state, in which the second extendable support element is not actuatable to expand; and
a tool for controlling the expansion of the first and second extendable support elements, wherein the tool is selectively positionable with respect to the body in one of a plurality of pre-defined positions, each of the plurality of pre-defined positions being defined by a different combination of activated and deactivated control states of the first and second extendable support elements.

17. The system of claim 16, wherein the tool is configured to actuate the expansion of the first and second extendable support elements.

18. The system of claim 16, wherein the implant further includes a channel configured to guide movement of the tool between the plurality of pre-defined positions.

19. The system of claim 16, wherein the first and second extendable support elements are configured to be extended by fluid.

20. A method of expanding a spinal implant positioned between a first vertebral body and a second vertebral body, comprising:
positioning a tool with respect to the spinal implant to a selected one of a plurality of pre-defined positions, wherein the spinal implant includes a body having a first surface for engaging the first vertebral body, a first extendable support element connected to the body at a first location, and a second extendable support element connected to the body at a second location, each of the first and second extendable support elements being operable between an activated control state, in which expansion of the respective extendable support element is controllable by the tool, and a deactivated control state, in which expansion of the respective extendable support element is not controllable by the tool, and wherein each of the plurality of pre-defined positions of the tool is defined by a different combination of activated and deactivated control states of the first and second extendable support elements; and
expanding at least one of the first or second extendable support elements such that the first or second end of the respective first or second extendable support element moves away from the body.

* * * * *